(12) United States Patent
Bravomalo et al.

(10) Patent No.: US 7,809,153 B2
(45) Date of Patent: Oct. 5, 2010

(54) SYSTEM AND METHOD FOR ASSESSMENT OF HEALTH RISKS AND VISUALIZATION OF WEIGHT LOSS AND MUSCLE GAIN

(75) Inventors: Mario J. Bravomalo, Arlington, TX (US); Russ Edward Brucks, Arlington, TX (US)

(73) Assignee: Inter-Images Partners, LP, Fort Worth, TX (US)

( * ) Notice: Subject to any disclaimer, the term of this patent is extended or adjusted under 35 U.S.C. 154(b) by 1590 days.

(21) Appl. No.: 10/684,023

(22) Filed: Oct. 10, 2003

(65) Prior Publication Data

US 2004/0131227 A1   Jul. 8, 2004

Related U.S. Application Data

(63) Continuation-in-part of application No. 09/560,243, filed on Apr. 27, 2000, now Pat. No. 6,643,385.

(51) Int. Cl.
*G06K 9/00* (2006.01)
(52) U.S. Cl. ...................................... 382/100
(58) Field of Classification Search ................. 382/164, 382/171, 173; 434/238
See application file for complete search history.

(56) References Cited

U.S. PATENT DOCUMENTS

| | | | |
|---|---|---|---|
| 4,602,280 A | 7/1986 | Maloomian | |
| 5,267,154 A * | 11/1993 | Takeuchi et al. | 345/473 |
| 5,673,691 A * | 10/1997 | Abrams et al. | 600/300 |
| 5,687,259 A | 11/1997 | Linford | |
| 5,825,941 A | 10/1998 | Linford | |
| 5,854,850 A | 12/1998 | Linford | |
| 5,963,214 A | 10/1999 | Cok | |
| 5,982,949 A | 11/1999 | Ohtsuka | |
| 5,986,671 A | 11/1999 | Fredlund | |
| 6,095,949 A | 8/2000 | Arai | |
| 6,336,136 B1 | 1/2002 | Harris | |

(Continued)

FOREIGN PATENT DOCUMENTS

WO    WO 0139089 A1 * 5/2001

OTHER PUBLICATIONS

Tiffany et al., Body Morph assessment , Februrary 21 2000, Obesity research vol. 9.pp. 43-50.*

(Continued)

*Primary Examiner*—Samir A. Ahmed
*Assistant Examiner*—Jayesh Patel
(74) *Attorney, Agent, or Firm*—Cox Smith Matthews Incorporated

(57) ABSTRACT

The present system combines image morphing technology, exercise programming, supplement sales, and motivational techniques into one product. Users begin by entering their current measurements, measurement goals and current picture into the system, preferably via a Web site. The picture is segmented into body components, and each affected segment is morphed based upon the measurements, goals, and the segment's responsiveness to weight loss in order to create a modified image representative of the user in a post-regimen condition. This system helps health and fitness businesses obtain new members and retain existing members by showing the members how they will look after following a specific regimen of diet and/or exercise. The system also predicts health risks of diabetes, heart disease, and stroke associated with the user's pre-regimen and post-regimen conditions.

9 Claims, 27 Drawing Sheets

U.S. PATENT DOCUMENTS

| | | | |
|---|---|---|---|
| 6,348,923 B2 | 2/2002 | Murata | |
| 6,502,583 B1* | 1/2003 | Utsugi | 132/200 |
| 7,184,047 B1* | 2/2007 | Crampton | 345/473 |
| 7,328,119 B1* | 2/2008 | Pryor et al. | 702/127 |
| 2002/0064302 A1* | 5/2002 | Massengill | 382/128 |
| 2002/0181752 A1* | 12/2002 | Wallo et al. | 382/130 |
| 2003/0013994 A1* | 1/2003 | Rubinstenn et al. | 600/587 |
| 2003/0065278 A1* | 4/2003 | Rubinstenn et al. | 600/587 |
| 2003/0065588 A1* | 4/2003 | Rubinstenn | 705/27 |
| 2003/0108851 A1* | 6/2003 | Posa | 434/238 |

OTHER PUBLICATIONS

Relationship between weight loss and Body image—weight loss treatment, Deborah Lynn Reas, Dec. 2002, Dissertation, pp. 1-92.*

Efit, Efit MorphOver, Apr. 10, 2000, pp. 1-2, http://www./efit.com/morphover/.

Sound Feelings, Slim Photo Fitness Motivation Tool, Apr. 10, 2000, pp. 1-4, http://www.soundfeelings...native_medicine/weight_loss/fitness.htm.

The Cleveland Clinic. Weight Cycling, Mar. 2002, pp. 1-2, http://my.webmd.com/medical_information/condition_centers/weight_control/default.htm.

Adami, Hans-Olov and Trichopoulos, Dimitrios. Obesity and Mortality from Cancer, The New England Journal of Medicine, Apr. 24, 2003, pp. 1623-1624, vol. 348:17, www.nejm.org.

Denoon, Daniel. Beginner Workout Tip: Smash the Mirror, Jun. 2003, pp. 1-2, http://my.webmed.com/content/Article/72/81520.htm.

Berkley, Cherie. The Higher Cost of Heavier Employees, Jul. 30, 2003, pp. 1-2, http://my.webmd.com/content/Article/71/81439.htm.

Support Manual for the Visual Fitness Planner, Document Version 1.3, Version 3.8.2; dated May 2002 (37 pages).

Description of Visual Fitness Planner Software Version 3.8.2; Licensed by Applicant's Predecessor to Others for use in the U.S. on or about May 13, 2002 (2 pages).

Support Manual for the Visual Fitness Planner, Document Version 1.3, Version 3.8.4, dated Jun. 2002 (38 pages).

Support Manual for the Visual Fitness Planner, Document Version 1.7, Version 3.9.4, created Jul. 2008; mailed to licenses on or about Sep. 24, 2002; viewable by licensee with password issued on or about Oct. 16, 2002 (37 pages).

* cited by examiner

Figure 17

SYSTEM AND METHOD FOR ASSESSMENT OF HEALTH RISKS AND VISUALIZATION OF WEIGHT LOSS AND MUSCLE GAIN

CROSS-REFERENCE TO RELATED APPLICATION

This application is a continuation-in-part of U.S. application Ser. No. 09/560,243 filed on Apr. 27, 2000 now U.S. Pat. No. 6,643,385, which is incorporated herein by reference.

BACKGROUND OF THE INVENTION

1. Field of the Invention

This invention relates to visual image processing used to predict a subject's appearance after a given amount of weight loss or muscle gain and prediction of changes in health risks associated with such weight loss or muscle gain. This invention also relates to business methods employing a predictive image visualization system to attract and retain clients of service providers in the weight loss food program, fitness center, physical therapy, sports medicine, and weight control medical industries.

2. Description of the Related Art

Many people desire to decrease their body weight, especially their body fat content. Modern life styles include highly sedentary weekday routines such as computer-based desk jobs, low-exercise commuting routines such as transportation by private automobile, and high-fat, high-calorie food selections often eaten quickly or while "on the run." Besides genetic tendencies, these factors lead many people to be dissatisfied with their appearance.

The problem is so prevalent that billion dollar industries have evolved to help people overcome their body dissatisfaction, including packaged food programs such as Weight Watchers (™) and Jenny Craig (™), fitness and workout centers such as Bally's (™), and physical therapy and sports medicine centers. This industry has also attracted medical and osteopathic doctors who specialize in the use of diet, exercise, and sometimes prescriptive regimens to help their clients and patients achieve their weight and appearance goals.

According to marketLooks.com (™), there are currently over 24,000 health clubs in the United States with 40 million members generating over 12 billion dollars in revenue each year. In 1995, health clubs and private individuals spent 3.2 billion dollars on fitness equipment alone, and these revenues are expected to reach 4.9 billion, a 38% increase, by the year 2001. In 1996, $500 million was spent on meal replacements and protein drinks, and these sales are expected to grow by 30% over the next five years.

However, many people fail to meet their goals, despite their efforts and the amounts they spend. The two most common reasons people fail in their attempts to change their body weight and appearance are lack of understanding and motivation.

Client and Patient Education

Previous technologies, systems, and methods do not adequately provide for the education and understanding of how exercise and diet affect the physiology of a person, especially taking into consideration the person's frame size or "build" and metabolism. Some available technologies include the ability to scan a photograph or import an image of a client or patient from a digital camera and to digitally alter the image manually to produce an estimate of the client's future appearance.

Currently available systems and methods simply "shrink" an image, such as by hand manipulation and editing of a digitized photograph, also known as digital "retouching." However, different body builds will store fat in different amounts in various portions of the body, and different exercises will reduce and/or firm up different body areas unevenly. Additionally, certain features of the body will show little or no response to weight change. For example, if the width of an image of a leg is decreased by a certain percentage, the appearance of the knee will be changed. However, knees generally do not have a significant fat layer and thus have a minimum circumference at almost any weight. So, the resulting image would predict an overall thin appearance to a leg which is not physiologically achievable. Similar factors apply to other points in the body, such as the width of shoulders and hips and the circumference of joints. As this method is highly inaccurate, it does not provide the level of education a client or patient needs to understand why particular diets and exercises have been recommended and how to adjust and apply this information in the future.

In order to accurately predict a future appearance, many physiological factors must be taken into account with diet and exercise goals. Estimating the results of these changes is typically beyond the technical and medical education and skill sets of most staffers at weight loss packaged food program outlets and physical fitness centers, and such estimation may be highly labor intensive and expensive if performed by appropriately qualified health and medical professionals.

At present, there are a few relevant resources available on the Internet. One service, called MorphOver (™) from eFit of New York City, N.Y., provides a service in which users e-mail a digital photograph in JPEG format to the company's website without any body measurements, body fat data, or indicated goals, and the service returns a "slimmed" photograph file within a few weeks. The instructions indicate that the original or "before" photograph must be of the subject in dark clothing, in a certain position, and with a white background. Another on-line service offered by Sound Feelings Publishing of Reseda, Calif., is similar in that it only requires submission of a photograph without any data as to the subject's body fat, dimensions, or goals. Additionally, the advertisement for this service states that a digital photograph artist will spend at least two hours manually manipulating the photograph.

Client and Patient Motivation

There are very few credible, non-surgical remedies for rapid weight loss. Therefore, successful weight loss programs require months to even years of commitment and adherence to prescribed diet and exercise regimens. If a client or patient becomes unmotivated or loses confidence in a program, he or she will not continue the program. Further, this client or patient may produce negative effects on the attraction and retention of other clients and patients as they will report to their friends and acquaintances that the program is another "scam" or "doesn't work," or that a particular professional is not competent. This can lead to a decline in memberships of businesses which are membership-based.

Therefore, there is a need in the art for a system and method which accurately produces predicted images of a weight-loss client or patient. Such a system and method should be operable by persons of usual skill and education who are commonly employed in the package food program and fitness center industries. Further, there is a need in the art for this system and method to easily and quickly produce intermediate images, such as weekly or monthly predictions, in order to provide accurate and positive confidence reinforcement to the client or patient, thereby enhancing the likelihood that the client or patient will continue to abide by the program and ultimately achieve his or her goals. There also exists a need in the art for this system and method to be operable in a networked or an Internet-based form or in a single workstation form. Additionally, there exists a need in the art for a method of leveraging such a system to attract and retain clients and patients in this industry.

SUMMARY OF THE INVENTION

System Overview

The present system comprises a fitness profiler which helps users gain insight into their fitness plans and their projected outcomes and results. The present system combines image morphing technology, exercise programming, supplement sales, and motivational techniques into one product.

Users begin by entering their measurement goals and current picture into the system, preferably via an Internet web site. The system analyzes the user's data and produces a customized fitness plan by applying a "morphing" process to the "before view." The picture is sectionalized into body components which are highly responsive to weight loss and components which are less responsive to weight loss, and the amount of change in each body section is determined by physiological tables and formulae. The resulting modified "after view" image is then returned to the user, preferably by online communications such as e-mail.

The Image Analyzer

The combination of three-dimensional ("3-D") morphing technology with mathematical statistics is used to project fat loss and muscle gain and to produce projected fitness outcomes. The user's input data preferably includes skin fold, circumference, height, weight, BMR, and activity level. By entering the client's measurements into a mathematical formula, the user's picture can be morphed into the desired outcome. The combination of skin fold and circumference measurement produces an accurate morphing outcome for each user.

Business Method for Use of the Predictive System

The image prediction system in accordance with the present invention helps the fitness industry overcome two of their biggest problems: obtaining new members and retaining current members. People may decide to join or renew their membership with a specific health club because they offer the present image prediction system as a service. By showing members how they will look 10 pounds thinner, for example, and giving them a clear-cut, understandable plan on how to achieve it, businesses in this industry will generate a satisfied and loyal clientele.

The present image prediction system is useful for nationwide health clubs, diet centers, and exercise equipment manufacturers. Direct marketing to Internet users may also be employed, as the technology and methods lend themselves well to interfacing to the user via common web site and browser technologies. As such, Internet users who are looking to start a fitness program may have access to the present image prediction system via a web site.

BRIEF DESCRIPTION OF THE DRAWINGS

FIG. 17 is a screen display of personal information generated by computer software in accordance with the present invention.

DETAILED DESCRIPTION OF A PREFERRED EMBODIMENT

An image prediction system in accordance with the present invention is preferably an Internet-based fitness system and service, which helps the user meet his or her fitness objectives. However, it may be implemented as a stand-alone workstation for use within a health club facility or medical professional's office.

In general, users enter their measurements, goals and current picture into the system. The system analyzes the user's data, generates a daily fitness program to help the customer reach his or her goal, and produces an after-fitness program image of the user. By setting the goals at an intermediate level, intermediate results can be projected and visualized.

The system employs readily available image morphing technology, driven by specialized technology to sectionalize the image into body components and predict specific size changes based upon physiological formulae and data tables.

System Overview

Figure 1:
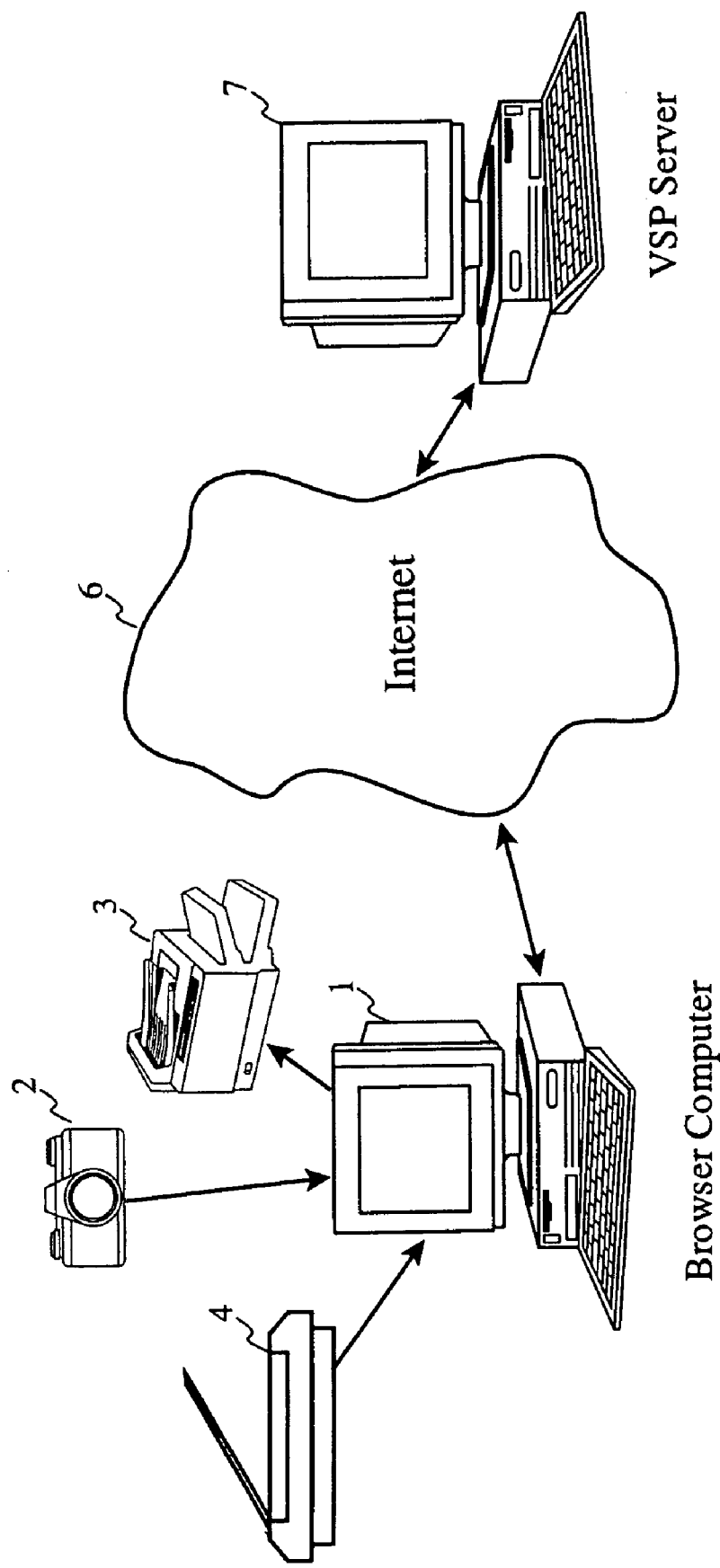
FIG. 1 shows the arrangement of an Internet browser computer, digital photography and scanning equipment, the Internet, and a system server in accordance with the present invention.

In a preferred embodiment, the user, health club advisor, or medical professional may use the system via a web site using a web browser, although in an alternate embodiment he or she may use the system directly. FIG. 1 illustrates the basic system components, including a browser computer (1) with Internet access (5), and a digital camera (2) or digital scanner (4), and optionally a printer (3). The computer can be any of several well-known and readily available systems, such as IBM-compatible personal computers running Microsoft's Windows operating system equipped with a web browser software such as Microsoft's Explorer or Netscape's Navigator, and appropriately equipped with a dial-up modem, cable modem, or Internet access via a local area network interface. Alternate computers, software and operating systems, such as Apple iMac, Unix and Linux, may be used equally well.

The system also preferably includes a computer network (6), such as the Internet or an intranet, and a server (7). This server (7) is preferably based upon any of the well-known, readily available Internet web server platforms, such as an IBM-compatible personal computer running Microsoft's Windows NT operating system and an Apache web server. The user may point his or her web browser to the address or Universal Resource Locator ("URL") of the server (7) to access web pages and forms, such as HTML, XTML, and Common Gateway Interface ("CGI"), all of which are well-known within the art. The user may transfer his or her "before" photo in the form of any of many well-known digital photograph formats, such as Joint Photographic Experts Group ("JPEG"), bitmap ("BMP") or tagged-image file format ("TIFF"), either by attachment to an e-mail message, retrieval by a Java client script (supplied by the server), by file transfer protocol ("FTP"), or any other suitable means.

Figure 2:
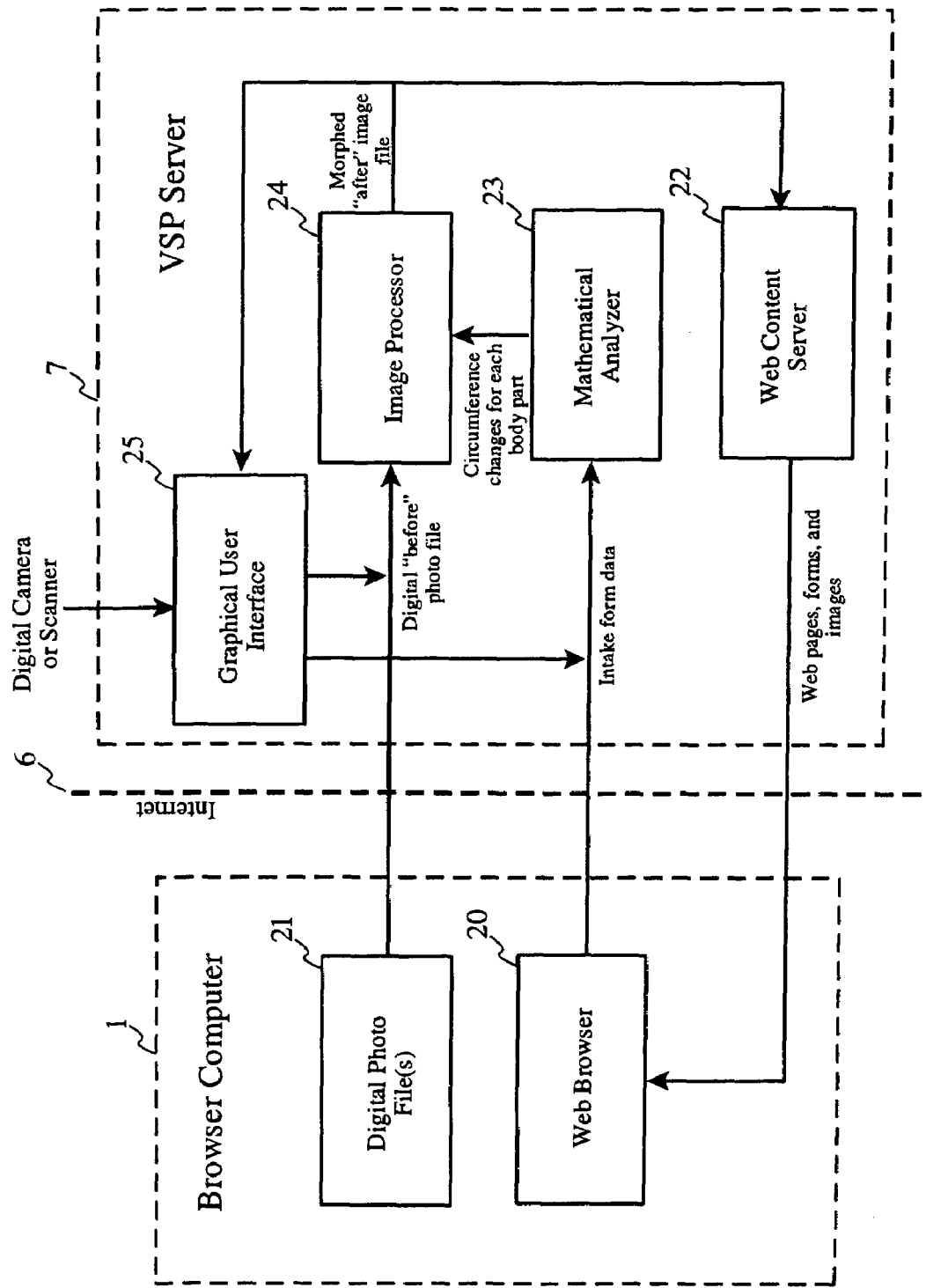
FIG. 2 illustrates in detail the functional organization of the system of FIG. 1.

FIG. 2 shows a preferred functional organization of the server system (7), which includes a web content server (22), a mathematical analyzer (23) and an image processor (24). In a preferred embodiment, the server system interfaces directly to the Internet using any of the well-known methods, such as by modem or local area network. The image processor (24) is described in more detail infra, as is the mathematical analyzer (23). If the system is implemented as a stand-alone workstation, it may also include a Graphical User Interface ("GUI") function for user control and input, such as a web browser software or custom GUI program. Additionally, for stand-alone use, a digital camera or scanner may be added to the system via a Universal Serial Bus ("USB") port, parallel port, or other common computer interface.

In a preferred embodiment, the user accesses the server (7) via an Internet (6) arrangement, using his or her browser computer (1). The web content server (22) transmits web pages, such as HTML and CGI forms, to the user to establish an account session and verify the user's identity, which are viewed and completed using a web browser (20). The user may then enter specific goals and measurement data and submit a "before" photographic image file. The goals and measurements may be entered using a client-side Java applet, Adobe Acrobat Portable Document Format ("PDF"), CGI form, or other suitable means, and the photo file (21) may be uploaded to the server (7) by e-mail attachment, FTP, a client-side script, or other suitable means.

The user's measurements and goals are received by the mathematical analyzer (23), wherein certain formulae and data tables are applied to determine the amount of exercise to achieve the weight loss goal, and the amount of circumferential reduction in each body section.

The user's "before" image file (21) is received by the image processor (24), as are the body segment circumference changes from the mathematical analyzer (23). The image processor (24) segments the photo into body sections, applies the reduction changes by morphing the photo, and produces the "after" image, which is then returned to the user by the web content server (22), preferably via a web page or e-mail attachment.

In the alternative, stand-alone embodiment, the "after" image is returned to the GUI (25) so that the operator and/or client or patient may view the projected results.

In practice, the goals may be adjusted to produce the desired results and/or intermediate results, thereby providing a full fitness plan needed to achieve the user's or client's goals.

Mathematical Analysis

The present system preferably requires measurements to be taken in order to produce a customized fitness plan. The desired measurements include:

(1) The circumferences of the neck, arm, chest, waist, hips, thigh, and calf.

(2) The skin fold of the neck, biceps, triceps, chest, scapula, abdomen, low back, hip, thigh, hamstring, and calf.

(3) The user's height, weight, and age.

(4) Percent desired of fat.

By taking the skin fold and circumference measurements, the present system utilizes the following new formula to find the circumference of the fat layer and predict the reduction in circumference for a particular body segment (all units are preferably in centimeters unless otherwise noted):

$$C_{change} = C_{after} - C_{before}$$

where $C_{change}$ is the change in circumference of a body part, $C_{after}$ is the final circumference of the body part after fat loss, and $C_{before}$ is the circumference of the body part at the beginning of the program.

Figure 3:
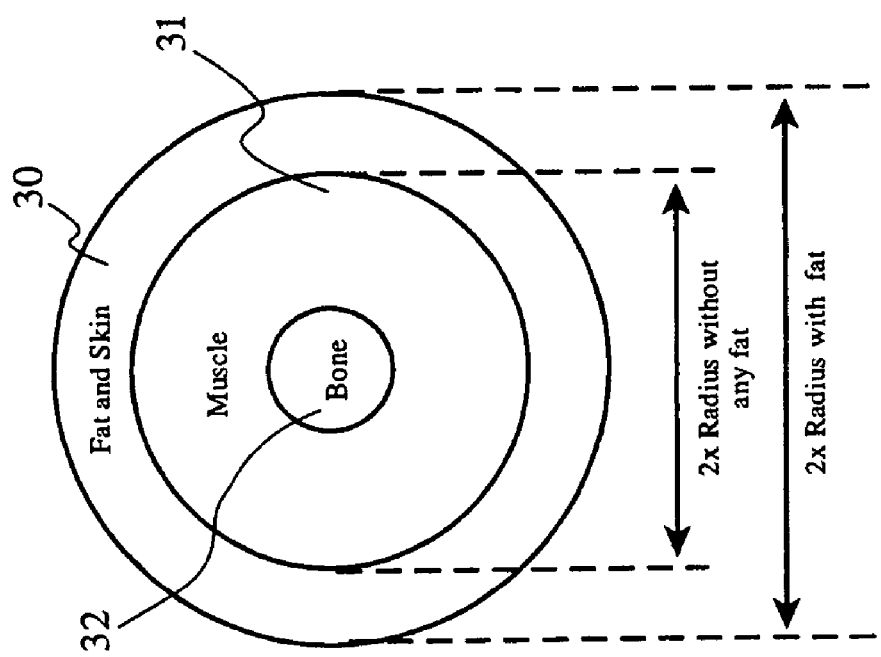
FIG. 3 depicts a cross-sectional view of a body portion to illustrate the calculation of base circumference of a body part.

FIG. 3 shows a cross sectional view of a body part, such as an upper arm or thigh, including a layer of fat with skin (30), a layer of muscle (31), and an underlying bone structure (32). The muscle and bone structure represent the component of the body part which will not be heavily affected by fat loss. Thus, the circumference of the body part without fat is calculated as:

$$\begin{aligned} C_{no\_fat} &= 2 \cdot \pi \cdot r_{no\_fat} \\ &= 2 \cdot \pi \cdot [r_{start} - \text{twice the depth of fat}] \\ &= 2 \cdot \pi \cdot [C_{before}/2\pi - (2 \cdot \text{skin\_fold\_measurement})] \end{aligned}$$

where $C_{no\_fat}$ represents the minimum circumference of a body part with no fat, $\pi$ represents an approximation for the constant "pi," such as 3.14, $C_{before}$ represents the starting circumference (current circumference) of the body part, and "skin_fold_measurement" is the measurement of standard skin fold. All units are preferably in centimeters, although the formula holds for any unit of measure.

The body part circumference after a desired percentage fat loss is calculated as:

$$C_{after} = 2 \cdot \pi \cdot \{r_{no\_fat} - \text{twice the desired depth of fat}\}$$

$$= 2 \cdot \pi \cdot \{[r_{start} - \text{twice the depth of fat}] +$$

$$\text{twice the desired depth of fat}\}$$

$$= 2 \cdot \pi \cdot \{[C_{before}/2\pi - (2 \cdot \text{skin\_fold\_measurement})] +$$

$$[2 \cdot \text{skin\_fold\_measurement} \cdot (1 - P) \cdot V]\}$$

where $C_{after}$ is the circumference of the body part after the desired fat loss, P is the amount of desired fat loss expressed in decimal form (e.g., 10% desired loss would be 0.10), and V is a constant based upon the body part being analyzed. The V constant is drawn from a table, and provides the variability to account for different body parts being more responsive to weight loss than others. For example, a body part which is highly responsive to weight loss would have a V value close to unity, while other less responsive body parts would have a greater than unity V value. Table 1 shows the preferred values for V.

TABLE 1

Adjustment Variable for Each Body Part

| Body Part | Skin Fold | Rank Order | Variable (V) |
|---|---|---|---|
| neck | 3 mm | 9 | 1 |
| biceps | 4 mm | 8 | 1.1 |
| triceps | 14 mm | 6 | 1.5 |
| chest | 21 mm | 5 | 1.8 |
| subscapula | 19 mm | 4 | 1.7 |
| abdomen | 30 mm | 1 | 2.5 |
| hip | 24 mm | 3 | 1.9 |
| thigh | 27 mm | 2 | 2.0 |
| calf | 13 mm | 7 | 1.2 |

The variable number is dependent on the skin fold of each body part. The rank order gives the ability to place the skin fold measurements in an order that the variable members can be assigned. By ranking the skin fold measurements from greatest to least, the variable numbers can be assigned. This table can change depending on where a person stores their fat.

Method of Producing the Predicted Image

In a preferred embodiment, the following method is implemented in software. The programming language is of little consequence, as the required calculations can be performed by most well-known languages, including "C", Java, and "C++." The method comprises the steps of:

(a) Receive from intake data sheet all user information needed for analysis (i.e., skin fold measurements, age, height, weight, desired loss amount), and receive "before" photographic image file.
(b) Scale real-life measurements to picture size.
(c) Place photograph on grid.
(d) Convert intake data to reduction on photograph utilizing formula.
(e) Place locating grids of individual body parts on "before" image.
(f) Find outline of the individual body parts within locating grids.
(g) Apply reduction of the individual body parts using morphing function.
(h) Apply original "before" photo next to reduced "after" photo.

In the first step, receipt of data from intake data sheet, the software receives the user's name, age, current weight, height, and circumference measurements for the neck, arm, chest, abdomen, hips, thigh, and calf. The data also includes skin fold measurements for the neck, biceps, triceps, chest, subscapula, abdomen, hips, thigh, and calf. The data further includes the desired percent body fat goal.

In the second step, the measurements are scaled to the picture size by taking the person's height and dividing by picture height. Then, this ratio is multiplied by all other real life measurements to produce scaled measurements. For example, if a person is actually 5 feet 9 inches (69 inches), and the photograph submitted represents a 7 inch tall image, the scaling ratio is 69/7=9.8. So, all real-life measurements would be multiplied by the inverse of the scaling ratio to yield a scaled measurement set.

Figure 4:
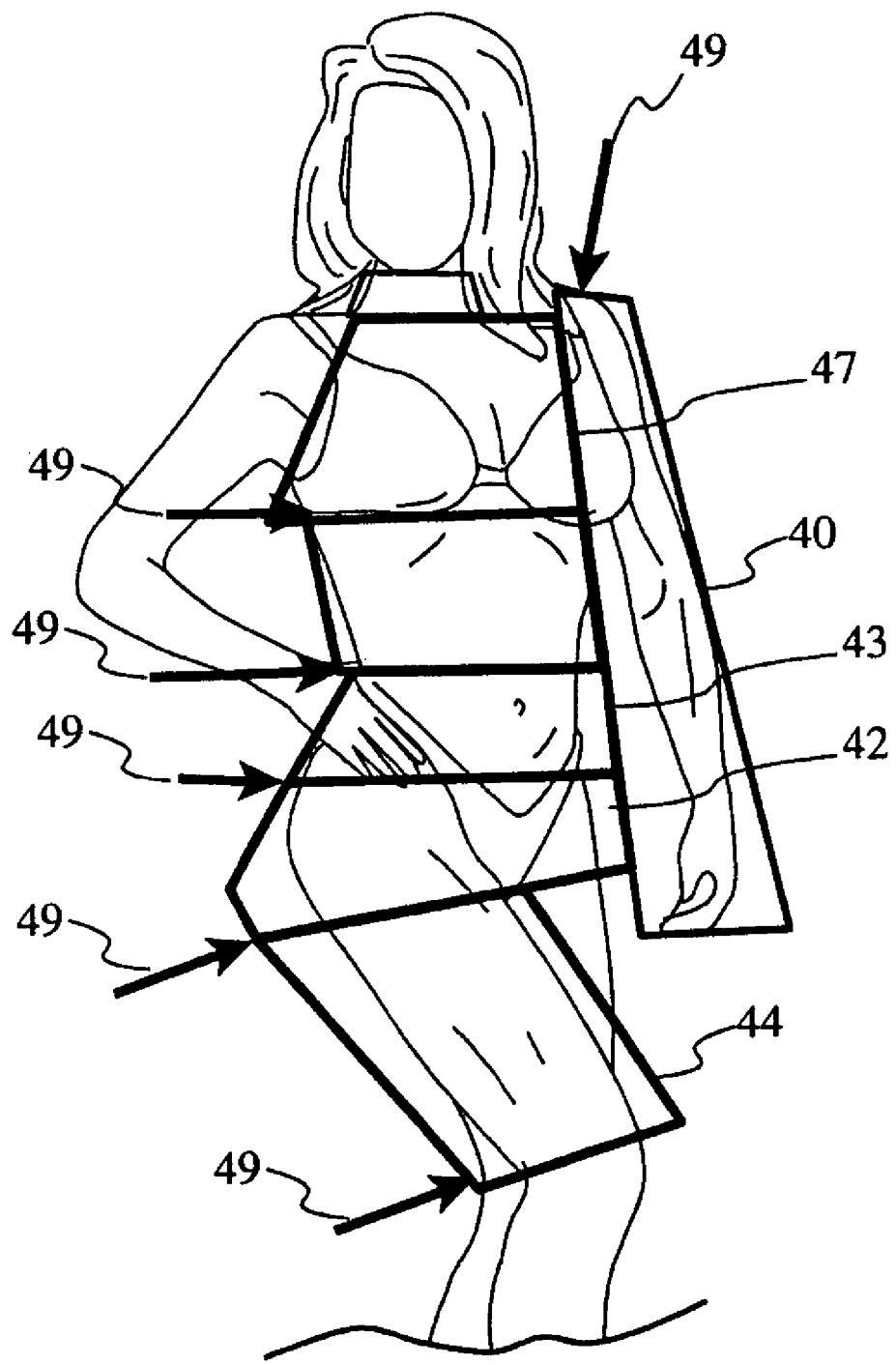
FIG. 4 sets forth an example of locating grids placed on a subject's photograph to aid the image processor in locating each body part.

In the third step, a locating grid is used to identify each body part, as shown in FIG. 4. Locating grids are placed on the arms (40), hips and/or buttocks (42), abdomen (43), thigh (44), calf (45), chest (47), and neck (46). In a preferred embodiment, a feature extraction algorithm may be used to automatically find each body portion, aided by the placement of arrows (49) on a background behind the subject at the time of taking the photograph. Alternatively, the body-part identifying grids may be placed on the photo manually through a graphical user interface. Both implementations are within the skill of the art of software engineers with expertise in this type of image processing.

Figure 5:
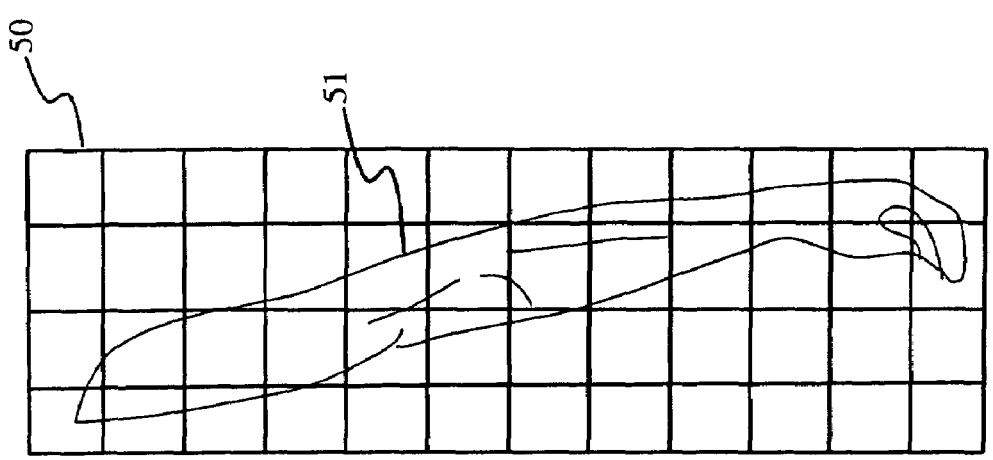
FIG. 5 shows the result of the placing of a grid over a single body part during the process of finding edges of the body part.

In the fourth step, a grid is overlaid on each body segment image, as shown in FIG. 5. The grid (50) is useful in the process in finding the edges (51) of the image of the body part and in applying a percent reduction to the image.

Figure 6:
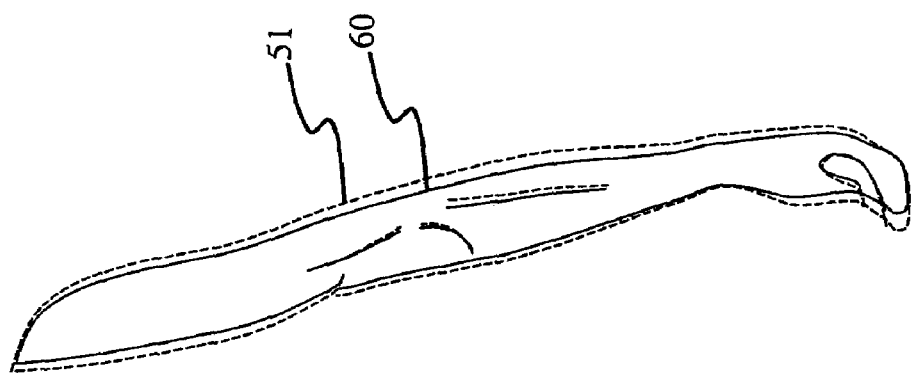
FIG. 6 illustrates the result of the morphing to reduce the width of the body part image.

In the fifth step, the reductions for each affected body segment are applied using an image morphing function, as shown in FIG. 6 with the new edges (60) of the body part image. This yields an "after" image in which each affected body part has been analytically reduced based upon each part's responsiveness to fat loss, the estimated beginning fat layer thickness based upon the skin fold measurements, and the desired amount of reduction of fat.

Figure 7:
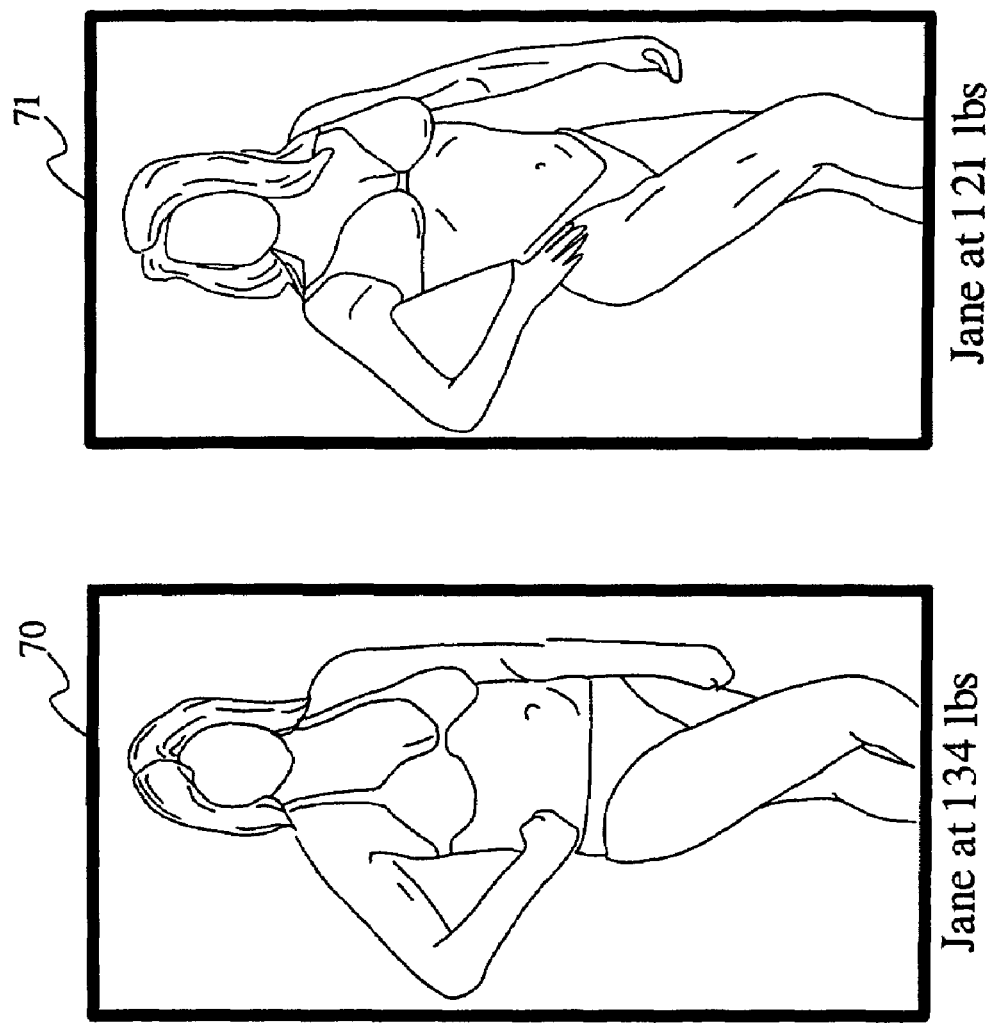
FIG. 7 shows a simulated side-by-side "before" and "after" comparison output from the system.

Finally, simulated "before" (70) and "after" (71) images are displayed side-by-side for ease of comparison, such as shown in FIG. 7. Thus, a more accurate system and method are provided which scales the current image of the client or patient on a segmented basis using physiological calculations.

Alternative Body Modeling Method

As an alternative to using actual photographic images of a person, a system in accordance with the present invention may utilize a stock or "canned" image of a generic person that may be customized to represent the salient features of the particular user by specifying a set of parameters. In this alternative embodiment, the present system preferably models body transformation in terms of muscle gain as well as fat loss, and the model is preferably three-dimensional. In order to make reasonable predictions, the system must begin with reasonable approximations of how much fat and muscle a person has initially. Preferably, a person's height, weight, age, and percent body fat are used to determine this starting point. To present this information visually, the system translates these physiological attributes into units that will cause the computer graphics model to present an image that is consistent with how one would expect a person with those attributes to look. Additionally, the system uses a description of the body shape to know where on the body to place the fat. For example, if the person is "pear-shaped" (represented by a triangle), the model will show most of the fat in the hips and thighs. If the person is shaped like an "apple" (represented by a circle), the model will concentrate the fat in the middle of the body. Finally, if the person has a "straight" body shape (represented by a rectangle), the model will distribute the fat more evenly. The overall effect is to create an image that is a good approximation of the person's initial appearance.

To build the body model, one of the first steps is preferably to determine how many pounds (or kilos) of fat the person would have if he or she had an amount of muscle consistent with that of a person who is currently not exercising or lifting weights. In terms of a preferred computer model, this means that the muscle layer is turned off or zero. This will yield a reasonable initial estimate of the person's percent body fat. If the user adjusts the percent body fat value, the system will modify the pounds (or kilos) of muscle and fat accordingly. These modifications will be translated into adjustments in the computer model's fat and muscle units. So, as the user increases the percent body fat, the model will grow "fatter," and as the user reduces the percent body fat, the model will grow more muscular.

The person's gender (male or female) is also generally an important factor because many relationships used in body modeling vary by gender. Additionally, the person's height and weight are important initial parameters. A set of equations is used to specify an optimal weight for any given height, depending on gender. By subtracting the optimal weight from the person's current weight, the system may establish an initial estimate of how many excess pounds of fat the person has available to lose. This determination of the amount of excess fat also enables the system to determine how much to inflate the fat layer of the model.

The optimal weight for a given height is given by the following equations, in which the units are inches for height and pounds for weight.

| Gender | Height Condition | Equation |
| --- | --- | --- |
| Male | All Heights | Ideal Weight = (4 × Height) − 100 |
| Female | Height > 66 inches (5 ft 6 in) | Ideal Weight = (4 × Height) − 131 |
|  | Height < 66 inches (5 ft 6 in) | Ideal Weight = (3 × Height) − 65 |

Figure 8:
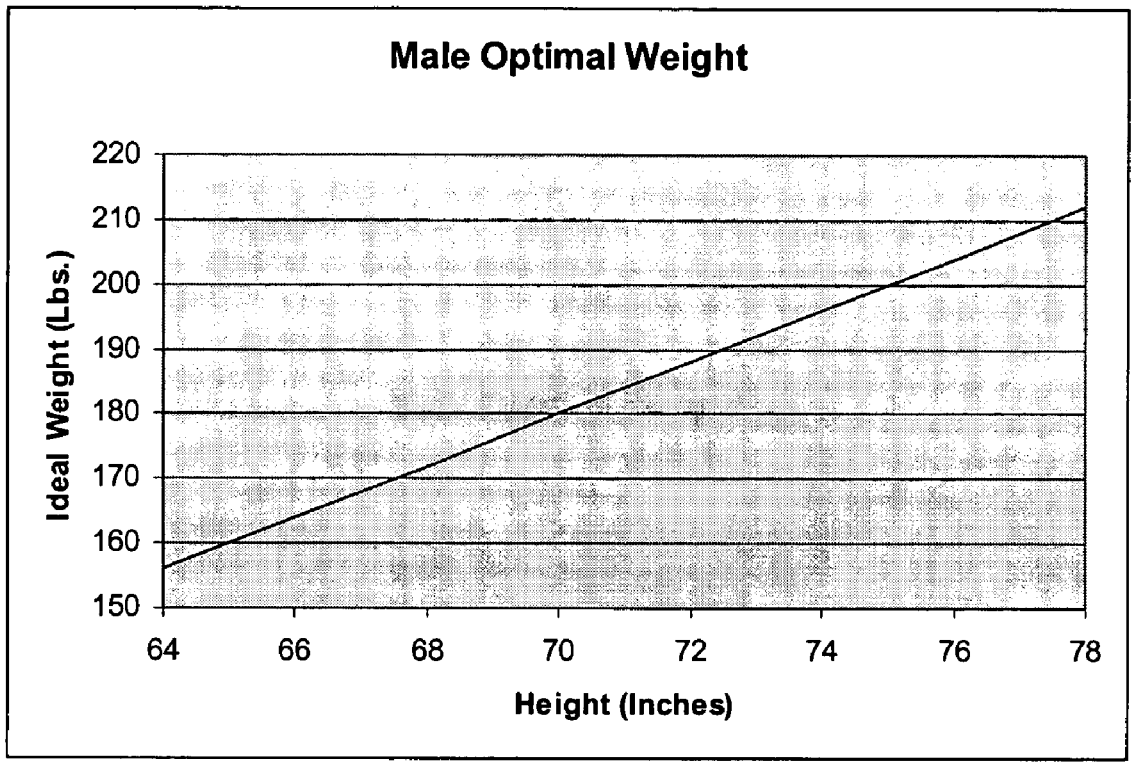
FIG. 8 is a graph of male optimal weight versus height.
Figure 9:
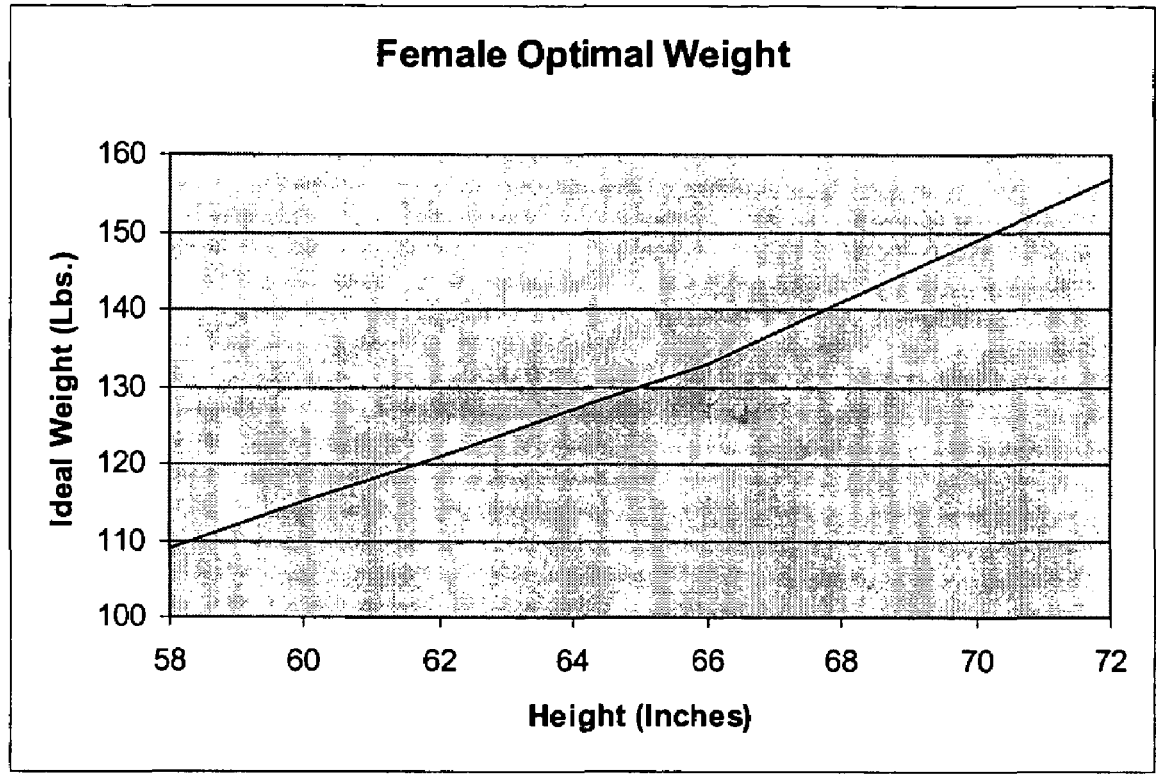
FIG. 9 is a graph of female optimal weight versus height.

These optimal weight equations are shown graphically in FIGS. 8 and 9.

In addition to the pounds of fat that can be lost through diet and exercise, there are some additional pounds of fat that are required by the human body. To estimate the percentage of body fat for a person, one must estimate essential fat as well as excess fat. By combining the estimated excess pounds of fat and the estimated essential pounds of fat, one arrives at an estimate of the total pounds of fat.

A person's amount of essential fat varies by age and may be estimated by the following equation:

$$\text{Essential Fat} = ((\text{Age} \times 0.001625) + 0.0425)(\text{Ideal Weight})$$

Figure 10:
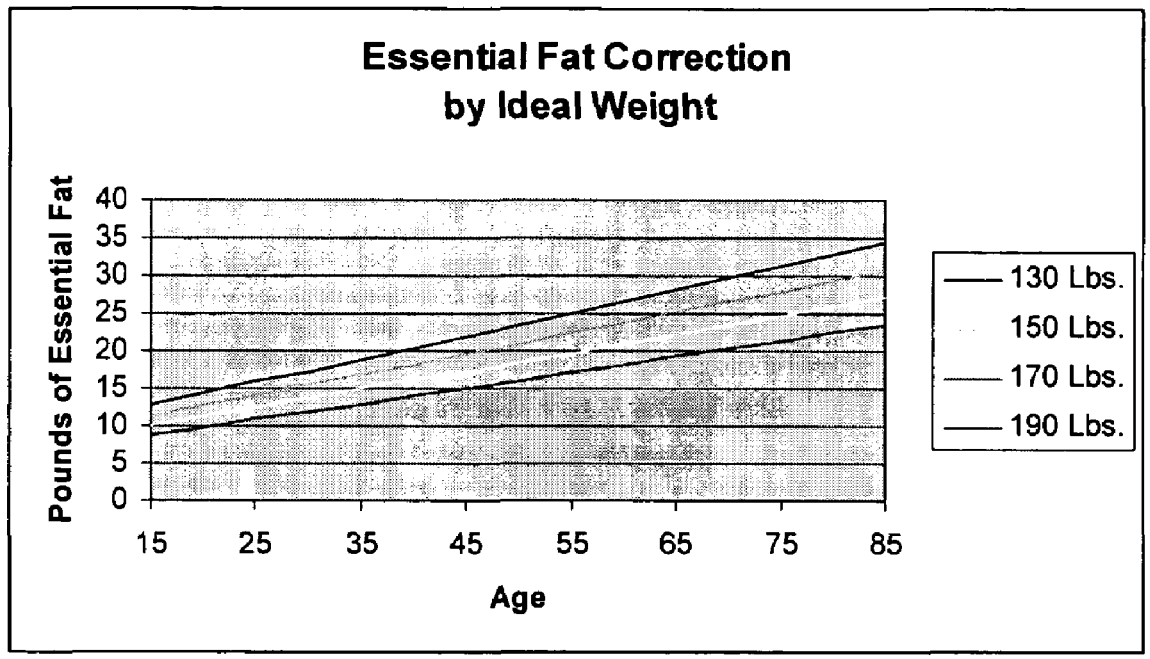
FIG. 10 is a graph of essential body fat versus age as a function of ideal weight.

This essential fat equation is illustrated graphically in FIG. 10.

To calculate the estimated body fat percentage, divide the pounds of fat by the person's current body weight as follows:

$$\text{Body Fat Percentage} = (\text{Essential Fat} + \text{Excess Fat}) / \text{Body Weight}$$

If the person is female, add 3%.

Preferably, a computer program in accordance with the present invention will not render an initial estimate of body fat percentage that is less than 4% for males or less than 7% for females, and the maximum estimated body fat percentage is preferably 61% for males and 64% for females.

Thus, by way of example, for a male who is 6 feet (72 inches) in height, 240 pounds in weight, and 40 years of age, his initial body fat may be estimated using the above equations as follows:

$$\text{Ideal Weight} = (4 \times 72 \text{ Inches}) - 100 = 188 \text{ Lbs.}$$

$$\text{Excess Pounds} = 240 \text{ Lbs.} - 188 \text{ Lbs.} = 52 \text{ Lbs.}$$

$$\text{Essential Fat} = ((40 \text{ Yrs}) \times (0.001625) + 0.0425) \times (188 \text{ Lbs}) = 20.21 \text{ Lbs.}$$

$$\text{Pounds of Fat} = 20.21 \text{ Lbs.} + 52 \text{ Lbs.} = 72.21 \text{ Lbs.}$$

$$\text{Percent Body Fat} = 72.21 \text{ Lbs.} / 240 \text{ Lbs.} = 30\%$$

Figure 17:
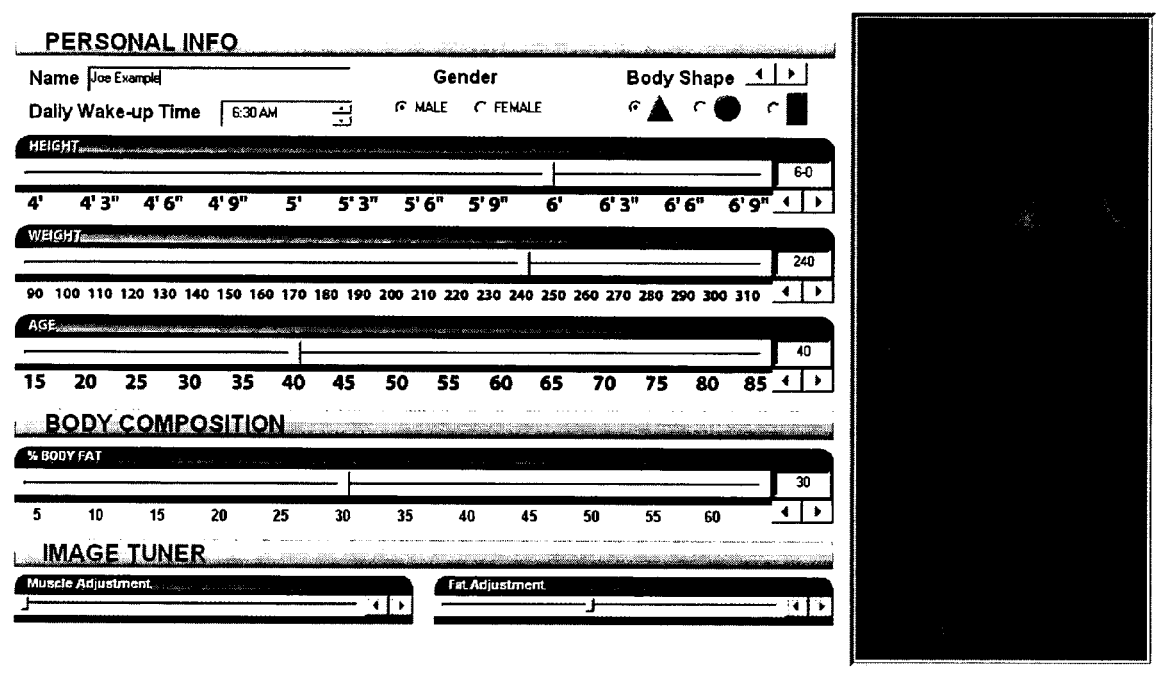

A preferred display screen corresponding to the foregoing example is shown in FIG. 17. The person's height, weight, age, and body fat are preferably selected by slider bars or entered in dialog boxes as shown in FIG. 17, but such parameters may be entered in any other suitable manner.

Figure 11:
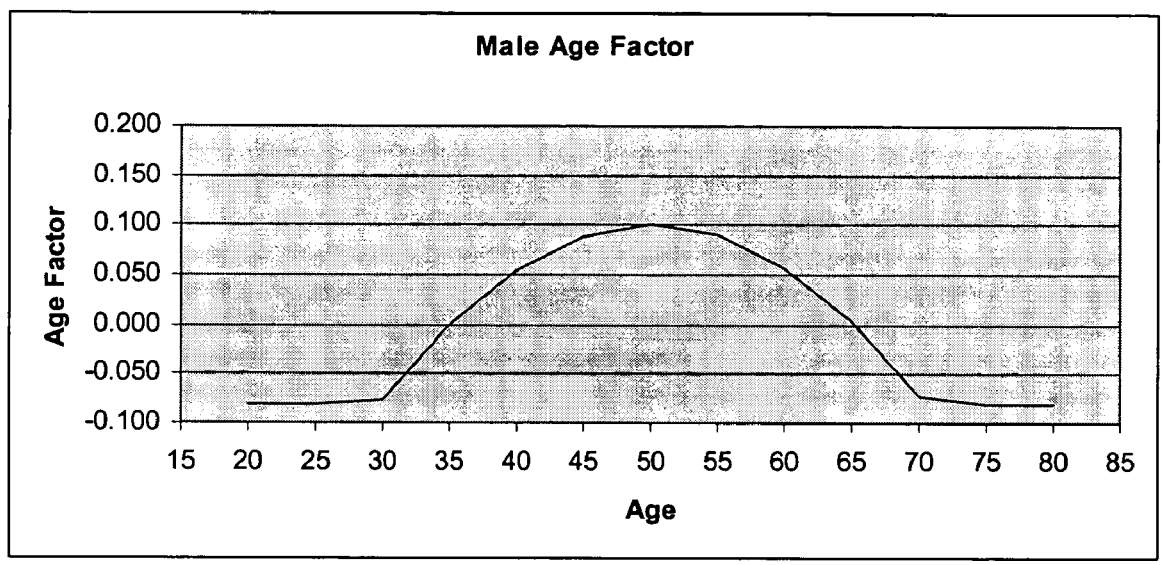
FIG. 11 is a graph of male age factor versus age.

A person's body appearance as well as the amount of fat for any given weight will vary depending on the person's age. The person's age is preferably used to make a small adjustment to the amount of fat that appears on the model for any given weight. This variation is preferably described by a parabolic function that applies between the ages of 30 and 70 as reflected in the following equation for males, which is depicted graphically in FIG. 11:

$$\text{Age Factor} = ((-0.000438)\text{Age}^2 + (0.0439)\text{Age}) - 1$$

Figure 12:
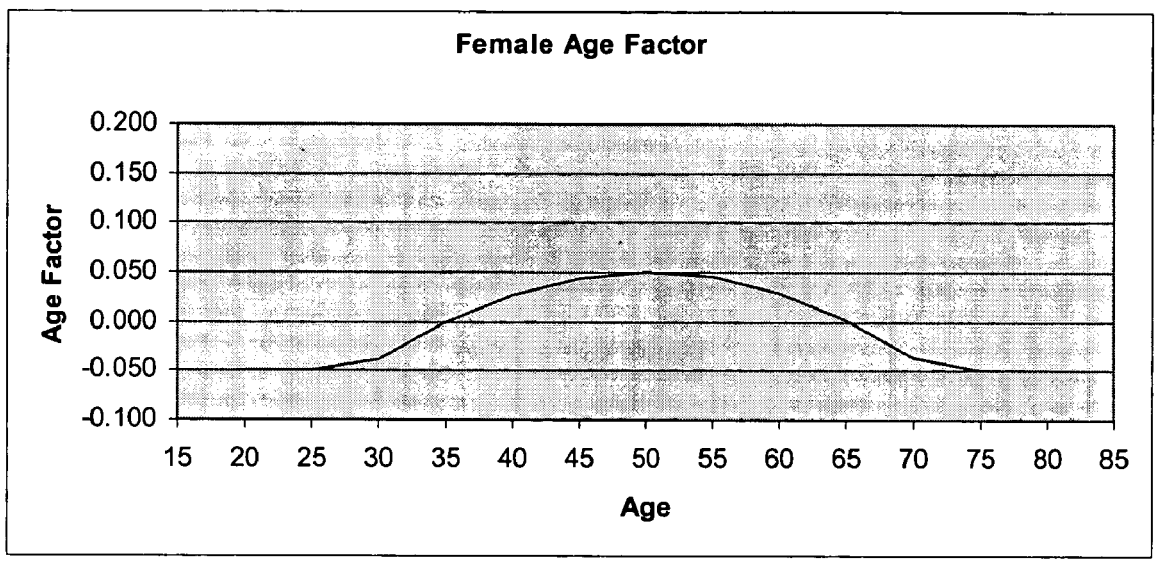
FIG. 12 is a graph of female age factor versus age.

A similar age factor relationship for females is depicted graphically in FIG. 12. For men, this age factor is preferably applied to boost fat pounds by up to 10% of a person's ideal weight. For women, the age factor is preferably applied to boost fat pounds by up to 5% of their ideal weight. For a middle-aged person, these additional pounds of fat will affect the appearance of the model. However, these additional pounds preferably are not assumed to be available for loss.

Thus, by way of example, considering again a 6 foot tall male who is 40 years of age, the weight adjustment for age is preferably calculated as follows:

$$\text{Age Factor} = ((-0.000438)(40)^2 + (0.0439)(40)) - 1 = 0.0552$$

$$\text{Age Pounds} = 188(0.0552) = 10.3776 \text{ lbs.}$$

This man's body model will then be shown with 10 more pounds of fat than would a similar person of age 35.

Figure 18:
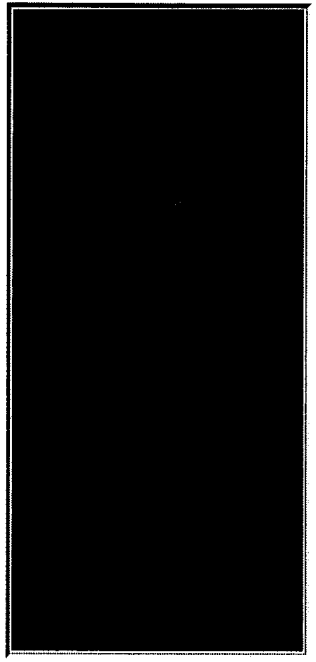
FIG. 18 is a variation of the screen display of FIG. 17.
Figure 19:
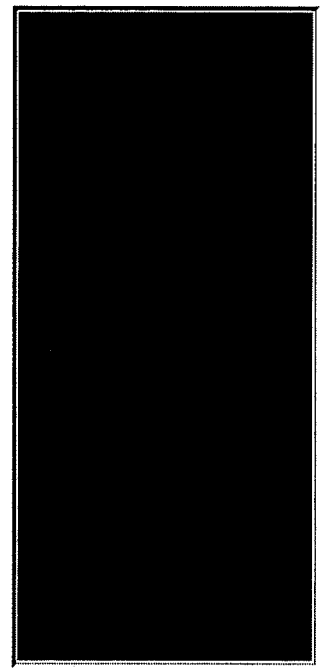
FIG. 19 is another variation of the screen display of FIG. 17.

A system in accordance with the present invention also preferably allows manual adjustment of the user's body fat percentage. After an initial estimate of body fat percentage has been calculated, the user may increase or decrease the body fat percentage by sliding the "% Body Fat" adjuster right or left (see FIGS. 17-19). This will have the effect of making the model "flabbier" or more muscular, as desired. When the user increases the body fat percentage, the software program increases the pounds of fat assumed for the given weight to reflect the new percentage. This also increases the number of pounds of fat available for loss. The fat layer of the model is inflated to reflect these additional pounds of fat.

> Pounds of Muscle Converted into Fat=(Body Weight)
> (Selected Body Fat %−Initial Body Fat %)

In the previous example, the 6 foot, 240 pound, 40 year old male was estimated to have a body fat percentage of 30%. If the user selects a body fat percentage of 37%, the model will reflect 16.8 more pounds of excess fat, as follows (see FIG. 18):

> Pounds of Muscle Converted into Fat=(240)(37%−30%)=16.8 Lbs.

If the user reduces the body fat percentage, the program converts pounds of fat (that were available for loss) into lean muscle mass to reflect the new percentage. As lean muscle is added, the muscle layer of the model is inflated to show greater muscle development. Additionally, the fat layer is reduced to reflect fewer pounds of excess fat.

> Pounds of Fat Converted into Muscle=(Body Weight)×(Initial Body Fat %−Selected Body Fat %)

In the previous example the 6 foot, 240 pound, 40 year old male was estimated to have a body fat percentage of 30%. If the user selects a body fat percentage of 25%, the model will reflect 12 more pounds of lean muscle and 12 less pounds of fat, as follows (see FIG. 19):

> Pounds of Fat Converted into Muscle=(240)×(30%−25%)=12 Lbs.

In addition, the muscle layer of the model and the fat layer of the model preferably may be adjusted independently by sliding the Muscle Adjustment or the Fat Adjustment slider bars. Increasing the Muscle Adjustor increases the appearance of muscle without modifying the weight or body fat percentage of the subject. Similarly, moving the Fat Adjustment will change the amount of fat displayed on the model without changing the weight or the pounds of fat available for loss. Moving these sliders modifies the default assumptions about how a pound of fat or a pound of muscle appears on a particular person. All subsequent modifications to the appearance of the model for this person will reflect these manual adjustments.

Health Risk Calculations

The present system also preferably estimates the risk of Type II Diabetes, Cardiovascular Heart Disease, and Stroke. Such disease risks are preferably calculated based on Body Mass Index (BMI), body fat percentage, and family history of disease. Age, gender, smoking, exercise, high blood pressure, and high cholesterol are also preferably taken into account. The calculated risk values are based on assumptions about the relative importance of several well known risk factors. The estimates of the magnitudes of each risk factor attempt to capture the prevailing wisdom about Type II Diabetes, Cardiovascular Heart Disease, and Stroke. Although quantifying a person's risk with a number in this manner does not imply the person's actual risk (rather, it indicates only that their risk could be higher or lower if certain factors were different), these calculations dramatically demonstrate how some behaviors increase disease risk while others reduce a person's risk of disease.

Figure 20:
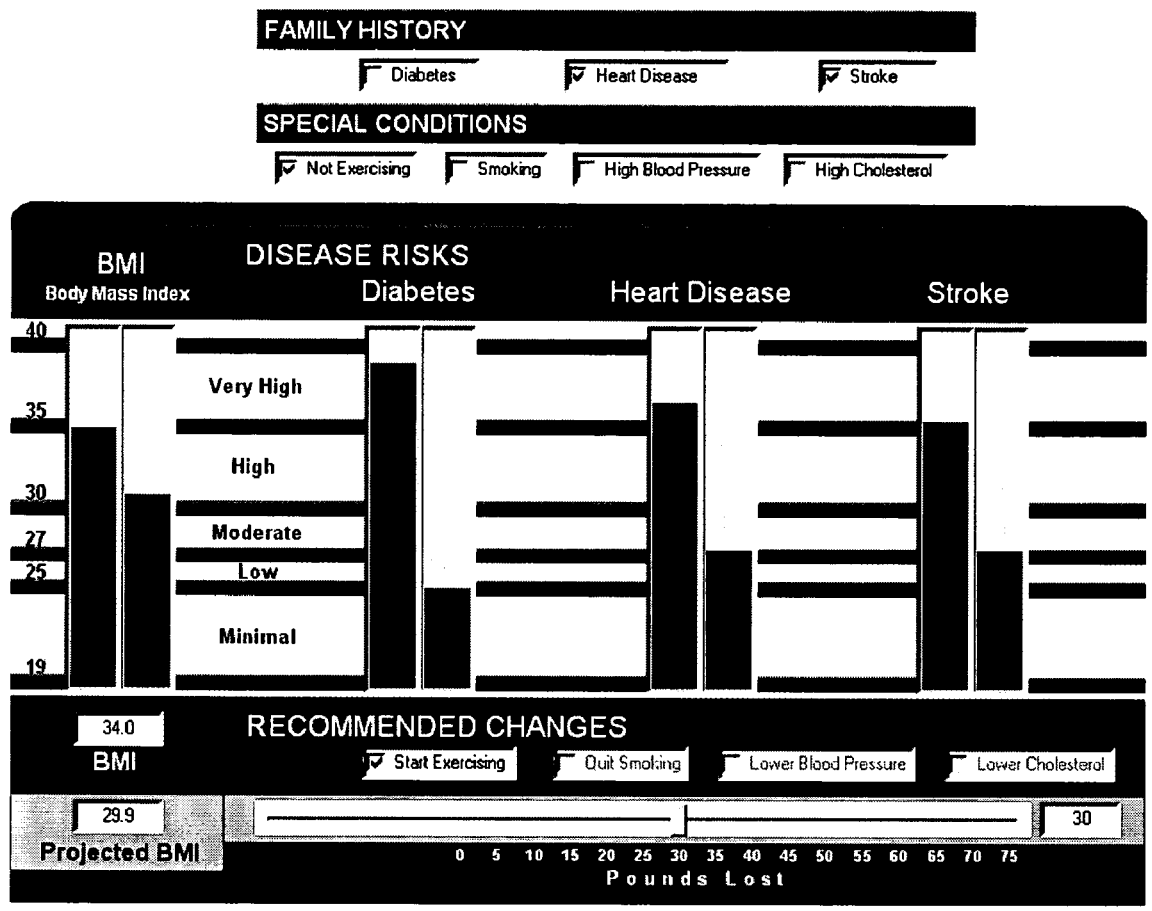
FIG. 20 is a screen display of health risks generated by computer software in accordance with the present invention.

As shown in FIG. 20, the person's BMI is preferably displayed with a vertical progress bar. The range of the BMI bar is preferably 18 to 40. Disease risk factors are preferably displayed with vertical progress bars having a range of 0 to 100. The level of risk is expressed by a value between 0 and 100, which may be qualitatively categorized as follows:

| Risk Value | Risk Category |
|---|---|
| 0-30 | Minimal |
| 31-39 | Low |
| 40-52 | Moderate |
| 53-75 | High |
| 76-98 | Very High |
| Over 98 | Extremely High |

The disease risk calculations preferably take into account the effects of body mass and body fat percentage on a person's health. The obesity factor is a combination of a person's BMI and a measure of their excess body fat. Excess body fat depends on a person's age and gender. The following table shows an acceptable amount of body fat for persons of various ages:

| Age | 20 | 40 | 60 | 80 |
|---|---|---|---|---|
| Male | 14 | 15 | 17 | 18 |
| Female | 17 | 18 | 19 | 21 |

To determine the excess body fat, the program subtracts the acceptable body fat percentage from the person's actual body fat percentage.

The obesity factor is preferably constructed from these basic functions:

| | |
|---|---|
| Body Mass Index (BMI) = | (Weight × 704.5)/Height × Height |
| BMI Factor = | (BMI − 25) × 7.5 |
| Acceptable Body Fat = | (Age × 0.0667 − 1.3333) + 14; (add 3 more if female) |
| Excess Body Fat Factor = | % Body Fat − Acceptable Body Fat |

The obesity factor is an average of the BMI factor and the Excess Body Fat Factor:

| | |
|---|---|
| Obesity Factor = | (BMI Factor + Excess Body Fat Factor)/2. |

Constructing the obesity factor in this way allows the present system to use the power of BMI to predict disease while also taking into account the effect of a high body fat percentage. The obesity factor is preferably scaled by the function:

$$Y=0.04X-0.28$$

This scaling function effectively lowers the calculated risks for athletes and others with a low percentage of body fat. If the BMI effect is a proxy for the amount of body fat a person carries, then if the person's body fat is known to be lower, then the effect of this factor should be smaller. For example, using this scaling function, the obesity factor for a person with 7% body fat would be scaled to 0. However, the obesity factor of a person with 32% body fat would be scaled by 100%.

Diabetes Risk Calculation

A person's risk of Type II Diabetes is the sum of six factors: family history, exercise, age, gender, BMI, and Percent Body Fat.

Family History
Add 15 if the subject has a family history of diabetes.
Exercise
Add 25 if the subject is not exercising.
Age
Add (Age/5)−7
BMI
Add 7.5 for every unit of BMI over 25% Body Fat
Add 1 for every percent of Excess Body Fat
Scales obesity factor by (4X−28)%

The obesity factor is magnified by 25% for Type II Diabetes.

By way of example, consider a female subject 5 ft. 6 in. tall, 175 lbs., 36 years old who has a family history of diabetes, does not exercise, has a BMI of 28.3, and has a body fat percentage of 35%. Her risk of Diabetes is calculated as follows (see FIG. 21):

| | | |
|---|---|---|
| Family History of diabetes | {0, 15} | 15 |
| Not Exercising | {0, 25} | 25 |
| Age | (36/5) − 7 = 0 | 0 |
| BMI Factor | 7.5 × (28.3 − 25)) = 24.75 | |
| Acceptable Body Fat | 17 + (36 × 0.07) − 1.3 = 18 | |
| Excess Body Fat Factor | 35 − 18 = 17 | |
| Obesity Factor | ((24.75) + 17))/2 = 20.9 | |
| Body Fat Scaler | 4(35) − 28 = 112% × 20.9 = 23.4 | |
| 25% Magnifier for Diabetes | 1.25 × 23.4 = | 29 |
| Diabetes Risk | | 69 |

Figure 21:
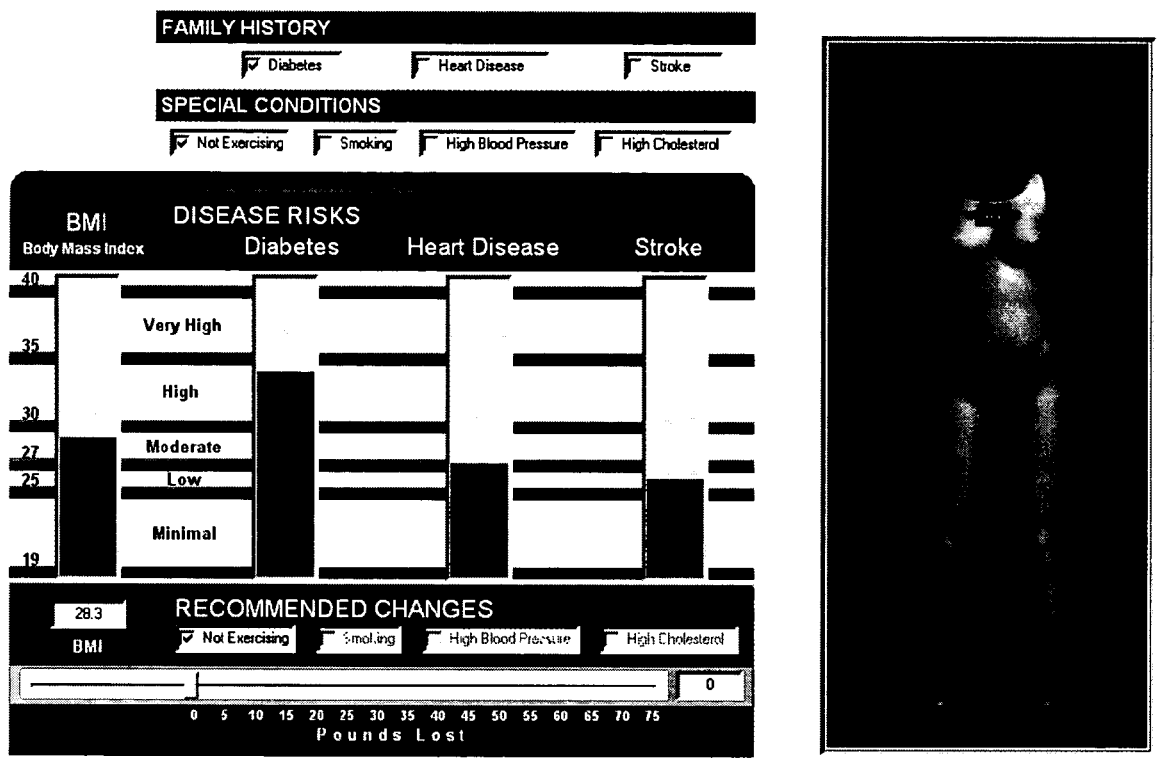
FIG. 21 is a screen display of health risks and an associated image for a female generated by computer software in accordance with the present invention.

A value of 69 places the subject in the "High" risk category, as depicted in FIG. 21.

Heart Disease Risk Calculation

Coronary Heart Disease Risk is the sum of nine factors: age, family history, gender, smoking, high blood pressure, exercise, BMI, and body fat percentage.

Age:
Add 1 for each year over 59 up to a maximum of 10 years.
Family History:
Add 15 if the subject has a family history of heart disease.
Add 5 if the subject has a family history of Diabetes.
Smoking
Add 25 if the subject smokes.
Gender
Add 5 if the subject is male.
High Blood Pressure
Add 15 if the subject has high blood pressure (greater than 120/80).
Exercise
Add 10 if the subject is not exercising.
High Cholesterol
Add 10 for high cholesterol (240 mg/dL or higher).
BMI
Add 7.5 for every unit of BMI over 25. % Body Fat
Add 1 for every percent of Excess Body Fat.
Scales Obesity factor by (4X−28) %

As an example, consider a male subject 6 ft. tall, 250 lbs., 62 years old who smokes and has a family history of heart disease. He does not have high blood pressure or high cholesterol. His BMI is 34.0. His Body Fat is 36%. His risk of heart disease is calculated as follows (see FIG. 22):

| | | |
|---|---|---|
| Age over 59: | 62 − 59 = 3 | 3 |
| Family History of heart disease | {0, 15} | 15 |
| Family History of diabetes | {0, 5} | 0 |
| Smoking | {0, 25} | 25 |
| Male Gender | {0, 5} | 5 |
| No High Blood Pressure | {0, 15} | 0 |
| Some Exercise | {0, 10} | 0 |
| High Cholesterol | {0, 10} | 0 |
| BMI Factor | 7.5 × (34.0 − 25)) = 67.5 | |
| Acceptable Body Fat | 14 + (62 × 0.07) − 1.3 = 17 | |
| Excess Body Fat Factor | 36 − 17 = 19 | |
| Obesity Factor | ((67.5) + 19))/2 = 43.25 | |
| Body Fat Scaler | 4(36 − 28 = 116% × 43.25 = | 50 |
| Heart Disease Risk | | 98 |

Figure 22:
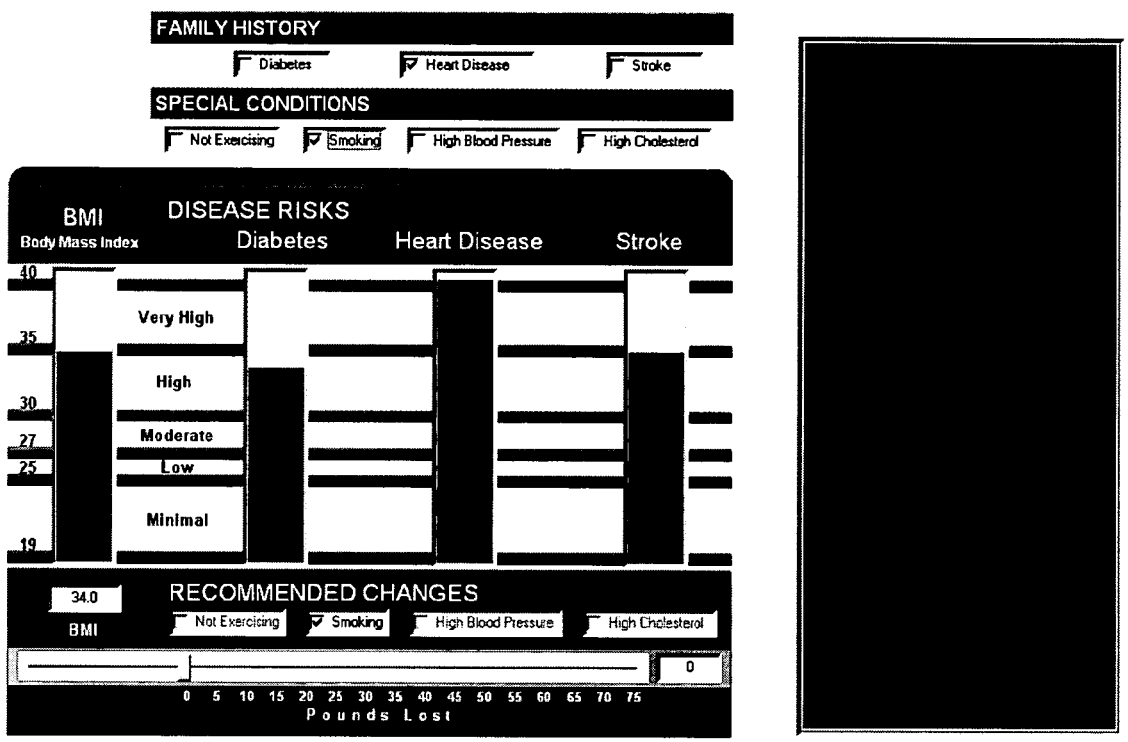
FIG. 22 is a screen display of health risks and an associated image for a male generated by computer software in accordance with the present invention.

A value of 98 places the subject in the "Very High" risk category, as depicted in FIG. 22.

Stroke Risk Calculation

Stroke risk is the sum of eight factors: age, family history, gender, smoking, high blood pressure, exercise, BMI, and high cholesterol.

Age:
Add 1 for each year over 59.
Family History:
Add 15 if the subject has a family history of stoke.
Add 5 if the subject has a family history of diabetes.
Smoking
Add 15 if the subject smokes.
Gender
Add 5 if the subject is male.
High Blood Pressure
Add 25 if the subject has high blood pressure (greater than 120/80).
Exercise
Add 5 if the subject is not exercising.
High Cholesterol
Add 10 for high cholesterol (240 mg/dL or higher)
BMI
Add 7.5 for every unit of BMI over 25% Body Fat
Add 1 for every percent of Excess Body Fat
Scales Obesity factor by (4X−28) %

As an example of stroke risk calculation, consider a female subject 5 ft. 3 in. tall, 165 lbs., 60 years old who smokes, has high blood pressure, is physically inactive, and has a family history of stroke. Her BMI is 29.3. Her Body Fat is 38%. Her risk of stroke is calculated as follows (see FIG. 23):

| | | |
|---|---|---|
| Age over 59: | 60 − 59 = 1 | 1 |
| Family History of Stoke | {0, 15} | 15 |
| Family History of diabetes | {0, 5} | 0 |
| Smoking | {0, 15} | 15 |
| Male Gender | {0, 5} | 0 |
| High Blood Pressure | {0, 25} | 25 |
| Not Exercising | {0, 5} | 5 |
| High Cholesterol | {0, 10} | 0 |
| BMI Factor | 7.5 × (29.3 − 25)) = 32.25 | |
| Acceptable Body Fat | 17 + (60 × 0.07) − 1.3 = 20 | |
| Excess Body Fat Factor | 38 − 20 = 18 | |
| Obesity Factor | ((32.25) + 18))/2 = 25.1 | |
| Body Fat Scaler | 4(38) − 28 = 124% × 25.1 = | 31 |
| Risk of Stroke | | 92 |

Figure 23:
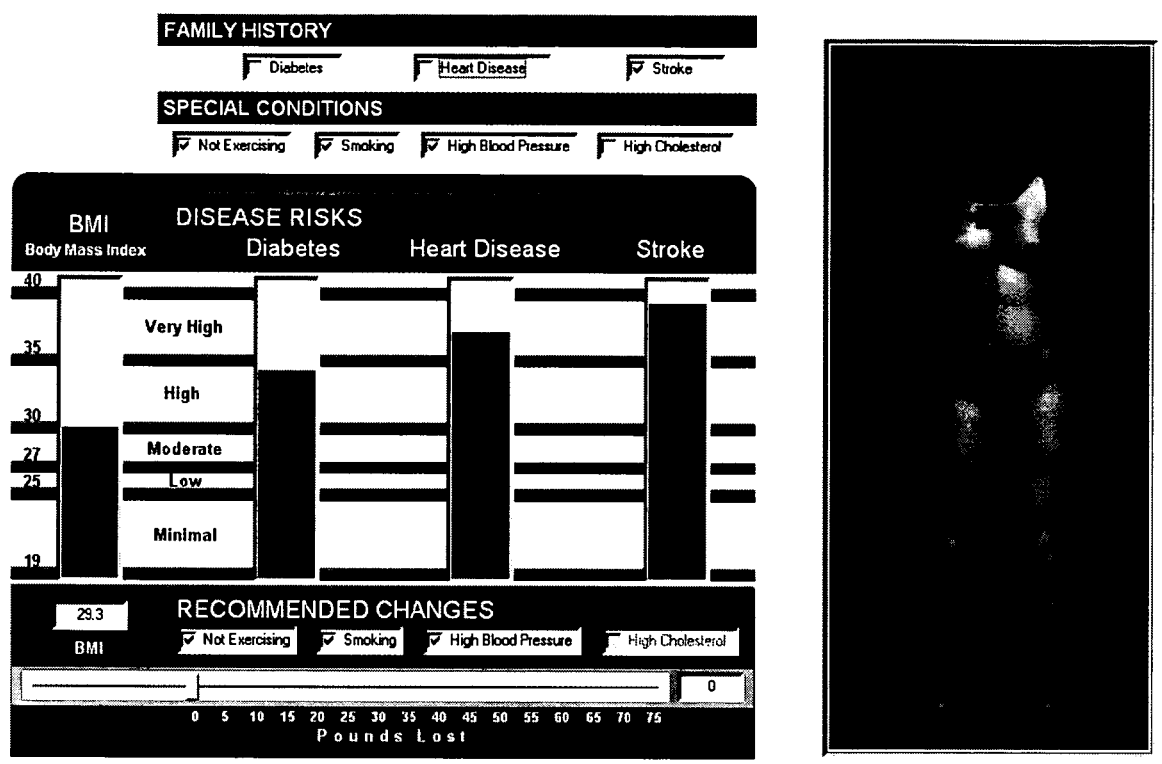
FIG. 23 is a variation of the screen display of FIG. 21.

A value of 92 places the subject in the "Very High" risk category, as depicted in FIG. 23.

Fat Loss Calculations

To predict how much fat will be burned over time, the present system treats the human body as a system that is constantly consuming energy. If a person takes in more energy (food) than the body can use, that surplus energy will be stored as fat. If a person uses more energy than is consumed, the body will convert stored fat into energy and that person will lose fat. A person can create an energy deficit by eating less or exercising more. It is this energy deficit that the present system calculates. When a user selects a certain number of days of compliance per week (or other suitable period of time) for eating and exercising according to plan, the present system adds up their caloric deficit for the week (or other suitable time period). According to well known data, it is assumed that one pound of fat is equal to 3,500 calories of energy. So, if a person can introduce a 3,500-calorie deficit within the course of a week, that person will lose one pound in one week.

It is assumed that the person's current physical condition is a result of their current eating and exercise habits. To recommend a dietary caloric deficit, the system first calculates how many calories are required per day to maintain the person's current weight. From that maintenance amount, subtracting an appropriate number of calories creates the desired dietary deficit. To find the initial maintenance value, the system preferably uses the standard calculation for Basil Metabolic Rate (BMR), as follows.

$$BMR_{female} = \text{Activity Rate} \times (665.1 + (9.56 \times \text{Weight}) + (1.85 \times \text{Height}) - (4.68 \times \text{Age}));$$

$$BMR_{male} = \text{Activity Rate} \times (66.47 + (13.75 \times \text{Weight}) + (5.0 \times \text{Height}) - (6.76 \times \text{Age})).$$

An Activity Rate of 1.3 (ambulatory) is preferably used to account for only their normal, daily activity. The effects of the exercise regimen are added separately. For example, a dietary deficit of 500 calories per day is found by subtracting 500 from the calculated BMR.

$$\text{Calories per Day} = BMR - 500 \text{ calories}$$

The present system provides three basic ways to create a caloric deficit: diet, resistance training, and cardiovascular training. Additionally, the present system allows the user to take into account the effects of dietary supplements and personal training in boosting the number of calories burned. The number of calories burned per week is the sum of five products:

Calories Burned/Week=(Daily Dietary Deficit calories×Days on Diet)+(Cardiovascular Exercise session calories×Days of Cardiovascular Exercise)+(Resistance Training session calories×Days of Resistance Exercise)+(Caloric value of a day of Supplementation×Days of Supplementation)+ (Caloric boost value of a day of Personal Assistance×Days of Personal Assistance)

The pounds of fat burned per week is found by dividing the Calories Burned per Week by the constant for Calories burned per Pound, as follows:

Pounds of Fat Burned/Week=(Calories of Fat Burned/Week)/(Calories/Pound)

The caloric value of a resistance training session or a cardiovascular exercise session varies with the intensity of the workout. Therefore, the value used in the calculations will vary depending on the type of exercise program selected. The user can vary the values used in these calculations by selecting different goals. In addition to the boost experienced while the personal trainer is present, the intensity of all solitary resistance training sessions is assumed to increase by some small amount.

Figure 24:
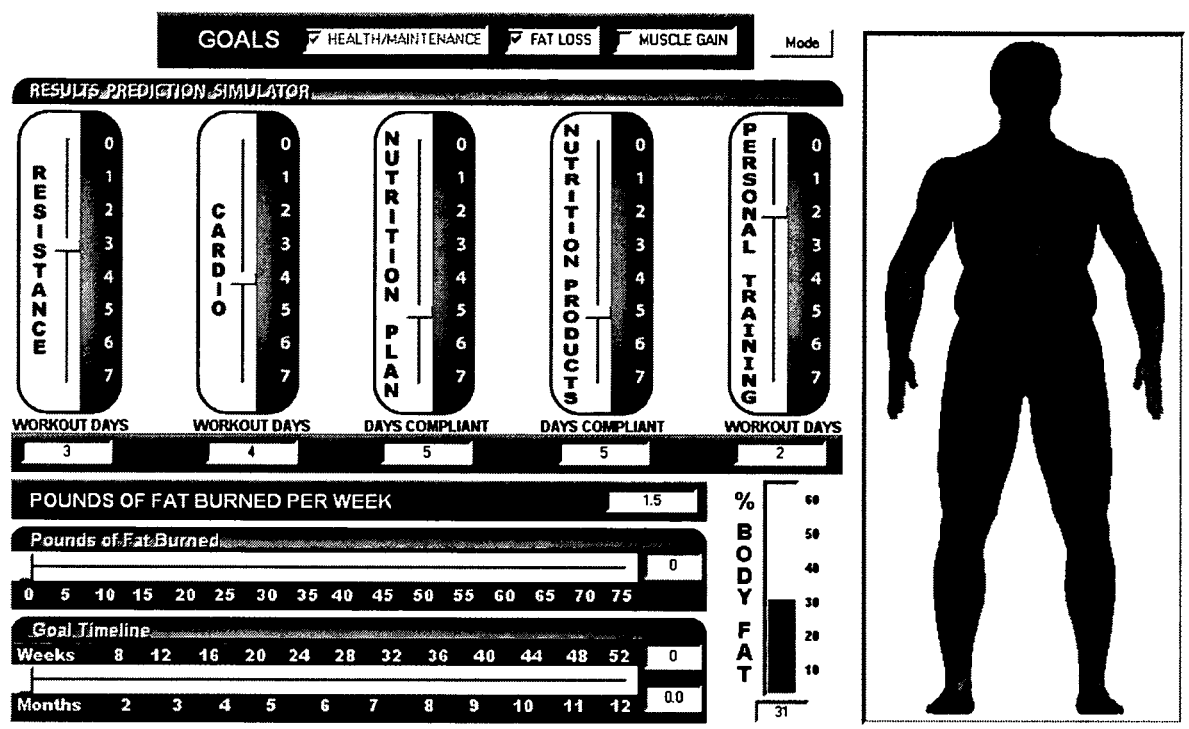
FIG. 24 is a screen display of diet and exercise goals and an associated image for a male before commencement of a desired regimen.

As an example, consider the following fitness program, which is graphically depicted in FIG. 24.

For the selected goal, the preferred caloric values used are as shown in the below table.

| Activity | Days of Compliance | Caloric Contribution | Total Calories |
|---|---|---|---|
| Daily Dietary Deficit = 500 Calories | 5 Days/Week | 2500 calories | |
| Caloric Value of Cardiovascular Exercise session = 300 calories | 4 Days/Week | 1200 calories | |
| Caloric Value of Resistance Training session (boosted by personal assistance) = 325 calories | 3 Days/Week | 975 calories | |
| Caloric Value of Dietary Supplementation = 100 calories | 5 Days/Week | 500 calories | |
| Caloric Value of Personal Assistance = 50 calories (while trainer is present) | 2 Days/Week | 100 calories | |
| Total Weekly Caloric Deficit | | | 5275 calories |

The fat burned as a result of this regimen is then calculated as follows:

Fat Burned=5275/3500=1.5 Lbs/Week

Given a rate of pounds burned per week, it is possible to calculate the number of pounds burned over a given period of time.

Lbs=Weeks×Lbs/Week

For example,

Lbs. of Fat Burned in 26 Weeks=26 Weeks×1.5 Lbs/Week=39 Lbs.

It is also possible to calculate how many weeks will be required to burn a particular amount of fat:

Weeks to burn 39 Lbs.=39 Lbs./1.5=26 Weeks

Figure 25:
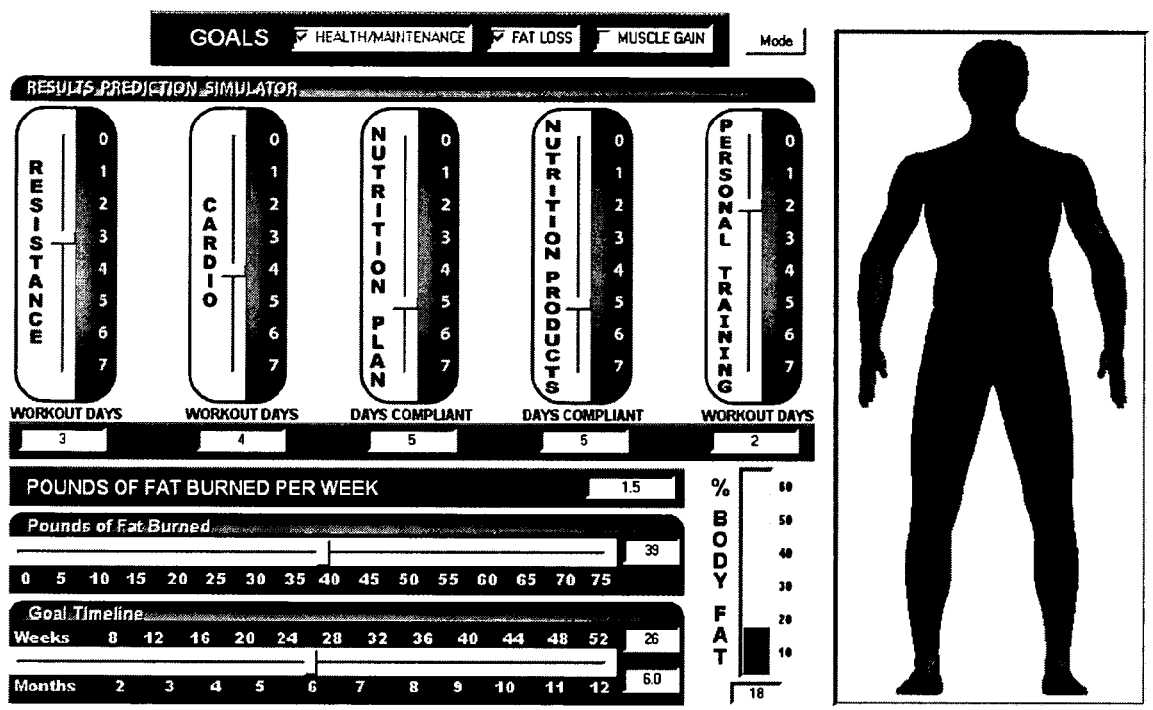
FIG. 25 is a screen display for the male of FIG. 24 after following the desired regimen for a period of time.

The present system will preferably calculate Weeks or Pounds, depending on which slider bar is "grabbed" by the user. If the user slides the "Pounds of Fat Burned" slider, the program will use the rate of fat burn to adjust the "Goal Timeline" Slider bar. Conversely, if the user slides the "Goal Timeline" slider bar, pounds of fat burned will be calculated. In either event, the body image will be slimmed to reflect the pounds of fat lost, as shown in FIG. 25. Also, the percent body fat display will be updated to reflect the new body composition.

The present system will preferably predict weight loss based on excess pounds of fat only. As described above, a person is assumed to have an optimal weight for any given height. Once all of the excess fat pounds are "lost," continued fat loss calculations are stopped. The present system preferably will not recommend weight loss below the assumed optimal weight, unless the person's body fat percentage indicates that additional excess fat pounds remain to be burned. Additionally, "age appearance adjustments," as discussed above, preferably remain in effect.

Muscle Gain Calculations

The present system preferably predicts muscle gain based on the person's age and gender as well as the muscle building program selected. The components affecting a muscle building program are nutrition, resistance training, and dietary supplementation. Preferably, it is assumed that the maximum amount of muscle will be gained by an 18 year old male. The amount of muscle gain will depend upon the number of days of resistance training, proper nutrition, and supplementation. The present system preferably calculates muscle gain in units that are native to the body model. The calculations are scaled to cause the body model's muscle to inflate with a rate that is consistent with what one would expect given a particular fitness program, and preferably in uniform proportions. The resulting muscle gain is transformed into pounds to display the pounds of muscle gained.

Base Muscle Gain Factor

The Base Muscle Gain factor represents the change in the appearance of the model after one resistance training session, if all other factors are at maximum. The magnitude of this factor changes depending on the goal selected by the user. For example, if the person's goal is to lose weight, the nutritional recommendations favor fat loss at the expense of muscle gain. However, if the person's selected goal is to gain muscle, the nutritional recommendations will favor muscle gain. Therefore, the magnitude of the Base Muscle Gain factor will be greater if one's goal is to gain muscle. Preferred Base Muscle Gain factors for various goals are listed in the table below.

| Goal | Base Muscle Gain Factor (model units) |
| --- | --- |
| Muscle Gain | 1/725 |
| Muscle Gain and Fat Loss | 1/1087 |
| Fat Loss | 1/1450 |
| Health/Maintenance | 1/1450 |

Supplementation Boost

Supplements are preferably assumed to boost muscle formation, depending on the number of days of supplementation and the number of days of resistance training. The default value for the supplement boost factor is preferably 15%.

Supplement Boost=1.0+((Days of Resistance Training/7 days)×(Days of Supplementation/7 days)×Supplement Boost Factor)

Resistance Training Compliance

Figure 13:
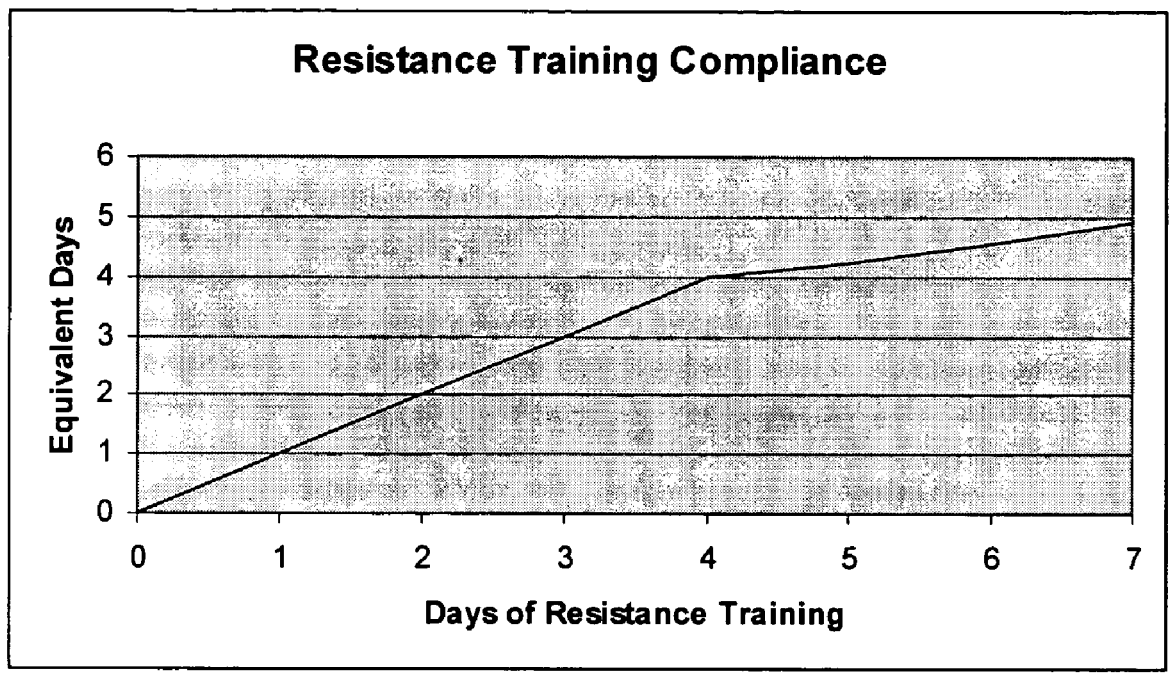
FIG. 13 is a graph of resistance training compliance by days.

As illustrated in FIG. 13, the effect of the number of days of resistance training is preferably assumed to be linear for up to 4 days per week. However, the effect of days 5, 6, and 7 are reduced by a function that compensates for the lack of rest days. Accordingly, Resistance Compliance is defined as follows:

If Days of Resistance training is greater than 4:

Resistance Compliance=(Days of Resistance Training/3)+2.56667

Otherwise

Resistance Compliance=Days of Resistance Training

Scaling Muscle Gain by Age

Figure 14:
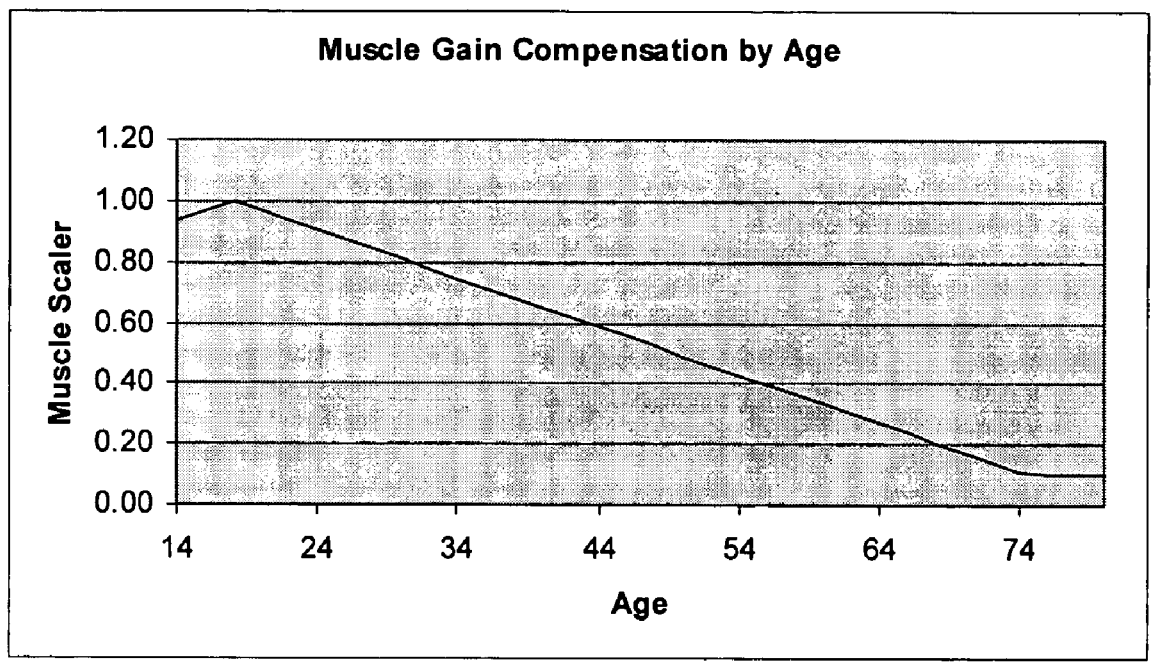
FIG. 14 is a graph of muscle gain compensation by age.

A 40 year old man, for instance, cannot build as much muscle in a given amount of time as he could have when he was 18, even though he engages in an identical fitness program. Therefore, the present system preferably scales the muscle response according to age, which is preferably accomplished in two steps. The first step preferably uses a function that peaks at age 18 and has a minimum value of 0.1, as shown in FIG. 14 and defined by the following equation. This function allocates the amount of muscle available for gain by age.

Age Compensation=Age×−0.015909+1.286364

A second function preferably transforms the scaling from model units into pounds gained according to the following equation:

Age Scaler=Age×−0.618182+65.7273

Figure 15:
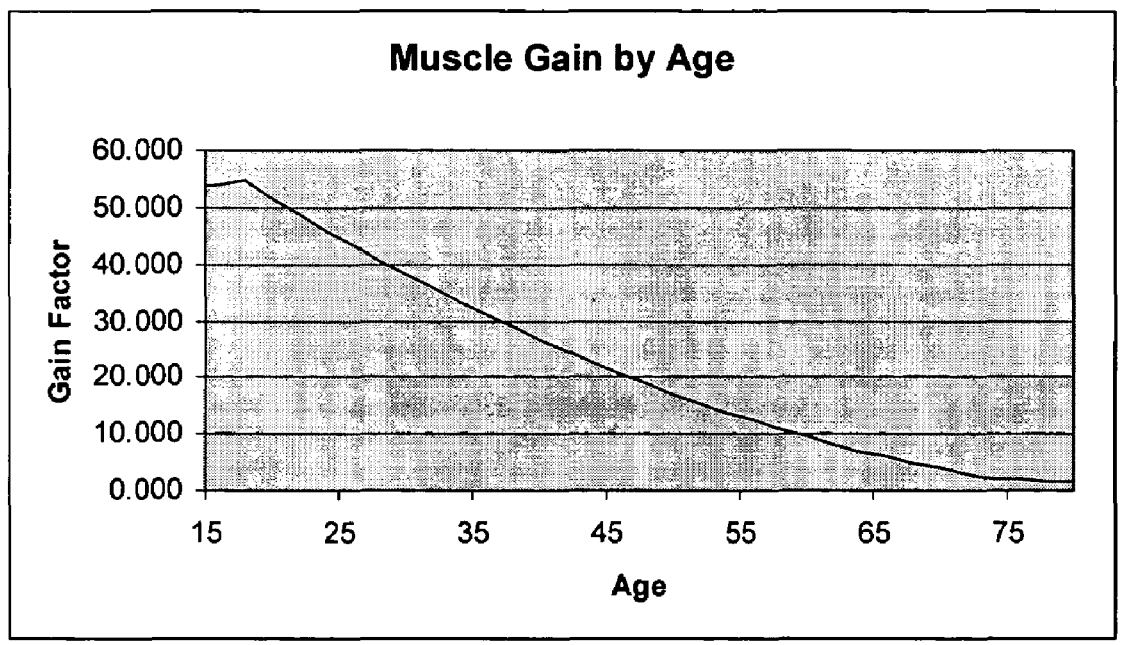
FIG. 15 is a graph of muscle gain factor by age.

Combining the two functions yields the preferred overall muscle gain by age curve as illustrated in FIG. 15 and defined by the following equation:

Age Factor=Age$^2$(0.009835)+Age(−1.84086)+84.54923

Scaling Muscle Gain by Nutritional Compliance

Figure 16:
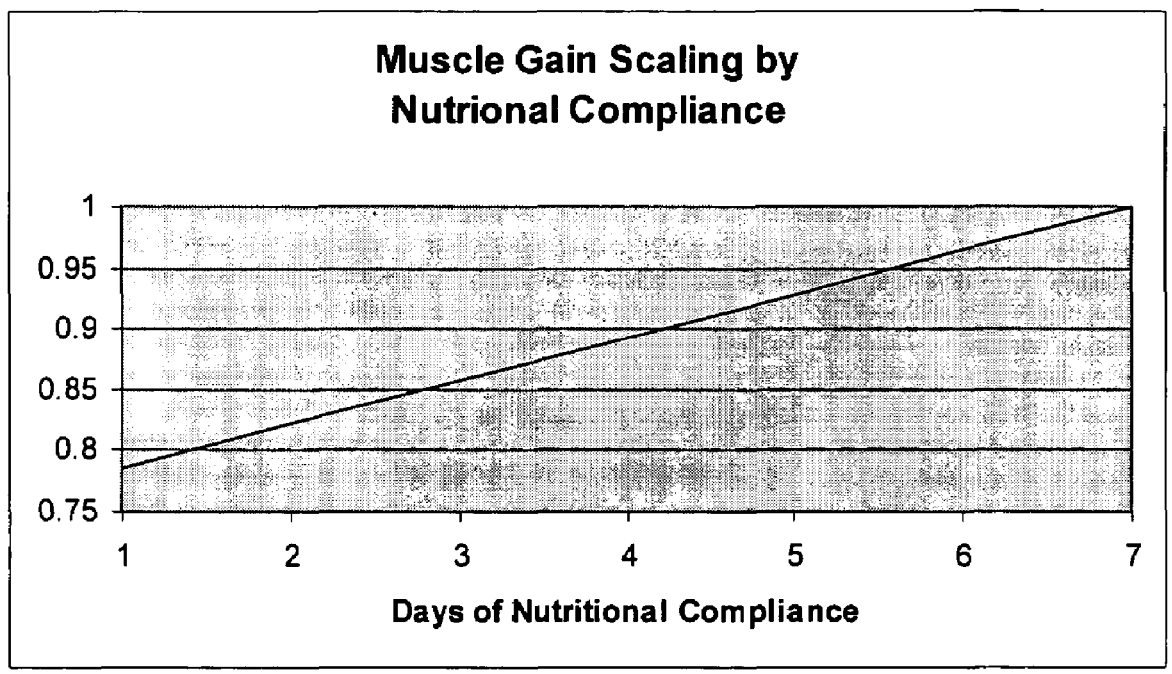
FIG. 16 is a graph of muscle gain scaling by nutritional compliance.

Proper nutrition is required to achieve maximum muscle gain. Therefore, days of inadequate nutrition reduce the amount of muscle gained. A Nutrition Factor is therefore preferably calculated by the following equation, which is depicted graphically in FIG. 16:

Nutrition Factor=Days/Week on Nutrition Plan (0.035714286)+0.75

Scaling Muscle Gain for Gender

Females are preferably assumed to be able to develop 55% as much muscle as males. For example, if a male can develop 11 pounds of muscle over one year on a particular fitness program, a female will develop 6 pounds over the same time using an identical fitness program. Accordingly, a Gender Factor is preferably established as follows:

Gender Factor$_{female}$=0.55

Gender Factor$_{male}$=1.0

Combined Scaling for Muscle Gain

As the user slides the Goal Timeline slider bar to the right, the present system calculates how much muscle is developed according to the fitness program selected, and the model image becomes more muscular. To determine how many pounds of muscle have been gained, the above scale factors are preferably multiplied together to determine the rate of muscle gain as follows:

Muscle Gained/Week=(Resistance Compliance×Base Muscle Gain Factor)×Supplement Boost×Age Factor×Nutrition Factor×Gender Factor The pounds of muscle gained over a number of weeks are found by multiplying the rate of gain by the time in weeks, as follows:

Muscle Gained in Lbs=(Muscle Gained in Lbs/Week)×Weeks

Figure 26:
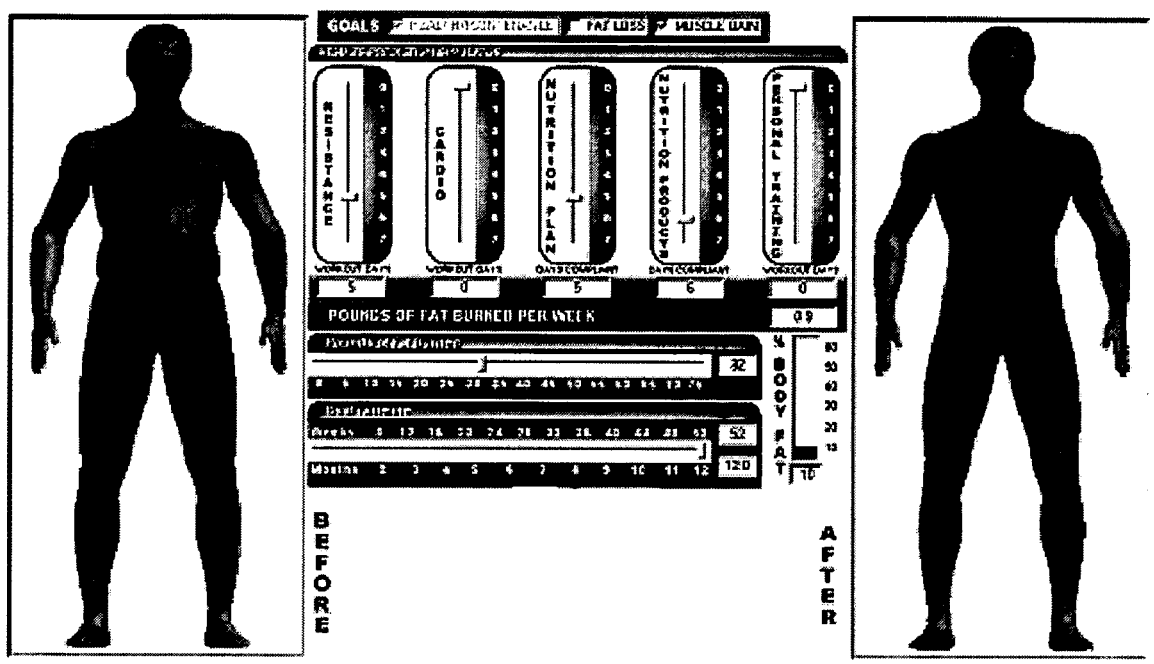
FIG. 26 is a screen display of diet and exercise goals and associated images for a male before commencement of a desired regimen and after following the desired regimen for a period of time.

As an example of a muscle gain calculation, consider a 220 pound, 40 year old male who eats properly 5 days per week, takes supplementation 6 days per week, and lifts weights 5 days per week as illustrated in FIG. 26. His primary goal is to gain muscle. To determine his muscle gain, the system first calculates all of the relevant scaling factors as follows:

Base Muscle Gain Factor=1/725

Supplement Boost=1.0+((5/7 days)×(6/7 days)×0.15)=1.09

Resistance Compliance=(5 days/3)+2.56667=4.2333

Age Factor=(40 yrs)$^2$(0.009835)+(40 yrs)(−1.84086)+84.54923=26.6508

Nutrition Factor=(5 days)(0.035714286)+0.75=0.9286

Gender Factor$_{male}$=1.0

Those factors are then combined to find the rate of muscle gain in pounds as follows:

$$\text{Muscle Gained/Week} = (4.2333/725) \times (1.09) \times (26.6508) \times (0.9286) \times (1.0)$$
$$= 0.1575$$

Finally, the number of weeks is multiplied by the muscle gain rate to find the total number of pounds of muscle gained as follows:

$$\text{Muscle Gained (lbs)} = (0.1575 \text{ Lbs/Week}) \times (52 \text{ Weeks}) = 8 \text{ Lbs.}$$

The pounds of muscle gained are preferably displayed for the user on a display screen showing before and after images as illustrated in FIG. 26.

Body Fat Percentage Recalculation

After a user has engaged in a fitness program over a period of time, the present system's body model composition will preferably change to reflect a loss of fat and/or a gain in muscle. Therefore, the body fat percentage should be recalculated. To recalculate the body fat percentage, the system should first determine the person's new body weight. The new body weight is found by subtracting the pounds of fat lost and adding the muscle gained as follows:

$$\text{Weight}_{new} = \text{Weight}_{initial} - \text{Fat Lost} + \text{Muscle Gained (Lbs)}$$

The system should also determine the pounds of body fat remaining. To do this, the known or assumed percent body fat of the person is used to determine how many pounds of fat the person currently has as follows:

$$\text{Fat}_{initial} \text{ (Lbs)} = \text{Body Fat Percentage}_{initial} \times \text{Weight}_{initial} \text{ (Lbs)}$$

The remaining pounds of fat are determined by subtracting the pounds of fat lost from the original pounds of body fat as follows:

$$\text{Fat}_{remaining} = \text{Fat}_{initial} - \text{Fat Lost (Lbs)}$$

The new body fat percentage is found by dividing the pounds of fat remaining by the new body weight as follows:

$$\text{Body Fat}_{new} (\%) = \text{Fat}_{remaining} \div \text{Weight}_{new}$$

Figure 27:
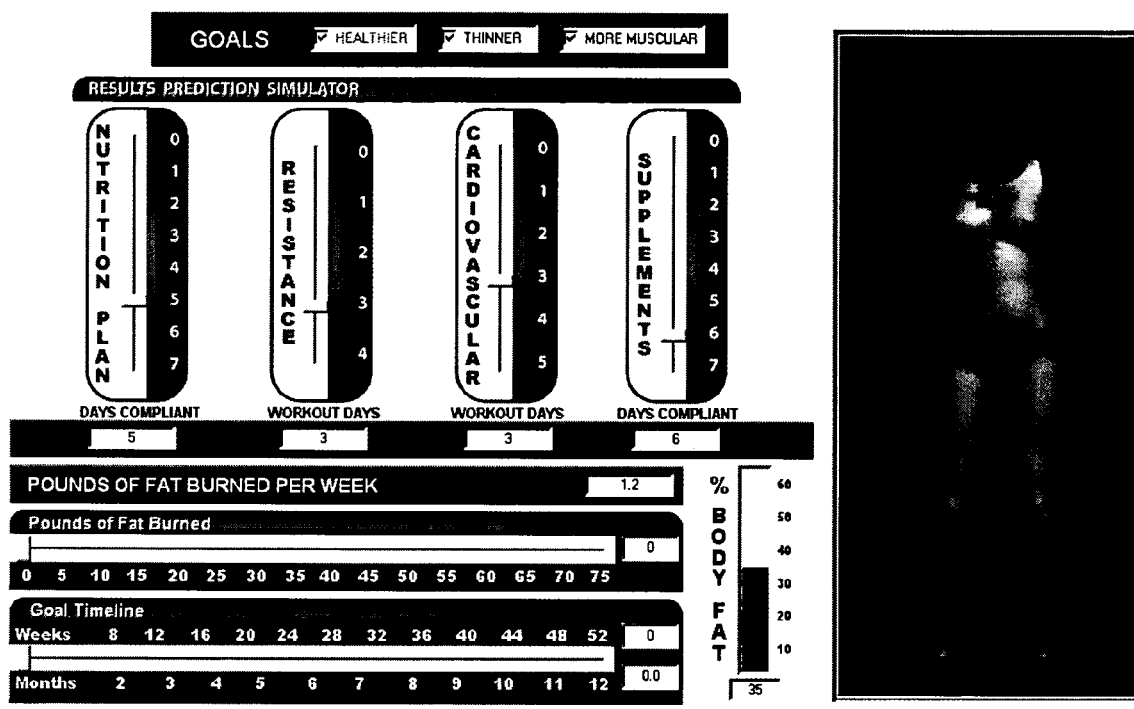
FIG. 27 is a screen display of diet and exercise goals and an associated image for a female before commencement of a desired regimen.

As an example, consider a 180 pound female with an initial body fat percentage of 35% as illustrated in FIG. 27. After engaging in a fitness program for 6 months, she loses 30 pounds of fat and gains 3 pounds of muscle. Her new weight is 153 Lbs.

$$\text{Weight}_{new} = (180 \text{ Lbs}) - (30 \text{ Lbs}) + (3 \text{ Lbs}) = 153 \text{ Lbs.}$$

Her initial pounds of fat were 63 Lbs.

$$\text{Fat}_{initial} \text{ (Lbs)} = \text{Bo}(35\%) \times 180 \text{ (Lbs)} = 63 \text{ Lbs.}$$

Her remaining pounds of fat are 33 Lbs.

$$\text{Fat}_{remaining} = (63 \text{ Lbs}) - (30 \text{ Lbs}) = 33 \text{ Lbs.}$$

Figure 28:
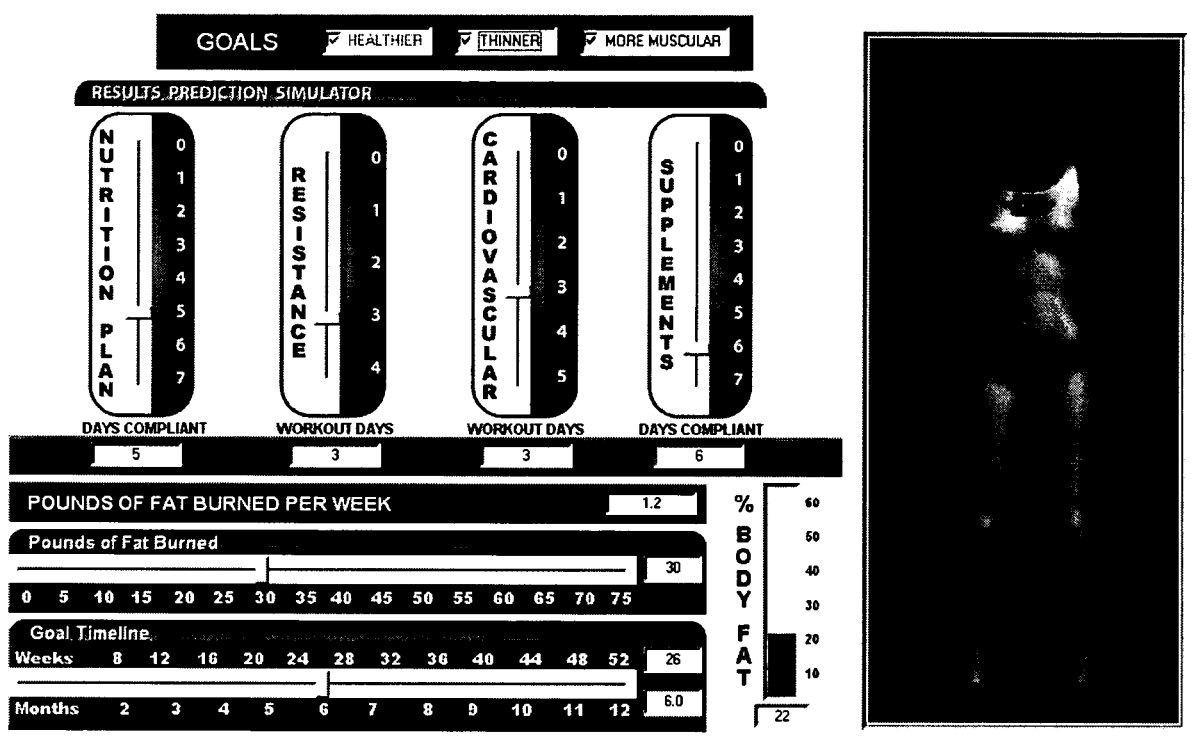
FIG. 28 is a screen display for the female of FIG. 27 after following the desired regimen for a period of time.

Therefore, her new percent body fat is 22%, as illustrated in FIG. 28.

$$\text{Body Fat}_{new} (\%) = (33 \text{ Lbs})/(153 \text{ Lbs}) = 22\%$$

Although the foregoing specific details describe a preferred embodiment of this invention, persons reasonably skilled in the art will recognize that various changes may be made in the details of this invention without departing from the spirit and scope of the invention as defined in the appended claims. Therefore, it should be understood that this invention is not to be limited to the specific details shown and described herein.

What is claimed is:

1. A method for producing an image predictive of a person's appearance resulting from following a prescribed regimen, said method comprising:
    receiving a first data set associated with said person;
    said first data set comprising a body shape designation;
    said body shape designation being representative of where fat is located on said person;
    creating a first image representative of said person in a pre-regimen condition by modifying a generic image based on said first data set;
    receiving a second data set comprising at least one goal desired from said regimen;
    creating a second image representative of said person in a post-regimen condition by modifying said first image based on said second data set;
    displaying said second image; and
    calculating an ideal weight and an estimated body fat percentage for said person; wherein said estimated body fat percentage is calculated substantially according to the following equation:

$$\text{Body Fat Percentage} = (\text{Essential Fat} + \text{Excess Fat})/\text{Body Weight}$$

said Essential Fat being calculated substantially according to the following equation:

$$\text{Essential Fat} = ((\text{Age} \times 0.001625) + 0.0425)(\text{Ideal Weight}).$$

2. A method for producing an image predictive of a person's appearance resulting from following a prescribed regimen, said method comprising:
    receiving a first data set associated with said person;
    said first data set comprising a body shape designation;
    said body shape designation being representative of where fat is located on said person;
    creating a first image representative of said person in a pre-regimen condition by modifying a generic image based on said first data set;
    receiving a second data set comprising at least one goal desired from said regimen;
    creating a second image representative of said person in a post-regimen condition by modifying said first image based on said second data set; and
    displaying said second image;
    wherein said creating a second image comprises calculation of an age factor; and
    wherein said age factor is calculated substantially according to the following equation:

$$\text{Age Factor} = ((-0.000438)\text{Age}^2 + (0.0439)\text{Age}) - 1.$$

3. A method for producing an image predictive of a person's a appearance resulting from following a prescribed regimen said method comprising:
    receiving a first data set associated with said person;
    said first data set comprising a body shape designation;
    said body shape designation being representative of where fat is located on said person;

creating a first image representative of said person in a pre-regimen condition by modifying a generic image based on said first data set;

receiving a second data set comprising at least one goal desired from said regimen;

creating a second image representative of said person in a post-regimen condition by modifying said first image based on said second data set; and displaying said second image;

wherein said at least one goal comprises muscle gain and wherein said muscle gain is calculated based on at least one of the following factors:

a base muscle gain factor;
a supplement boost factor;
a resistance compliance factor;
an age factor;
a nutrition factor; and
a gender factor;

wherein said base muscle gain factor is selected from the group consisting of:

$1/725$ if said goal comprises muscle gain only;
$1/1087$ if said goal comprises muscle gain and fat loss;
$1/1450$ if said goal comprises fat loss only or health maintenance.

4. A method for producing an image predictive of a person's appearance resulting from following a prescribed regimen, said method comprising:

receiving a first data set associated with said person;
said first data set comprising a body shape designation;
said body shape designation being representative of where fat is located on said person;

creating a first image representative of said person in a pre-regimen condition by modifying a generic image based on said first data set;

receiving a second data set comprising at least one goal desired from said regimen;

creating a second image representative of said person in a post-regimen condition by modifying said first image based on said second data set; and displaying said second image;

wherein said at least one goal comprises muscle gain and wherein said muscle gain is calculated based on at least one of the following factors:

a base muscle gain factor;
a supplement boost factor;
a resistance compliance factor;
an age factor;
a nutrition factor; and
a gender factor;

wherein a supplement boost is calculated substantially according to the following equation:

Supplement Boost=1.0+((Days of Resistance Training /7 days) ×(Days of Supplementation /7 days) ×Supplement Boost Factor).

5. A method for producing an image predictive of a person's a appearance resulting from following a prescribed regimen, said method comprising:

receiving a first data set associated with said person;
said first data set comprising a body shape designation;
said body shape designation being representative of where fat is located on said person;

creating a first image representative of said person in a pre-regimen condition by modifying a generic image based on said first data set;

receiving a second data set comprising at least one goal desired from said regimen;

creating a second image representative of said person in a post-regimen condition by modifying a generic image based on said first data set; and displaying said second image;

wherein said at least one goal corn rises muscle am and wherein said muscle am is calculated based on at least one of the following factors:

a base muscle gain factor;
a supplement boost factor;
a resistance compliance factor;
an age factor;
a nutrition factor; and
a gender factor;

wherein said resistance compliance factor is calculated substantially according to one of the following:

(a) if said regimen comprises a number of days of resistance training per week which is greater than 4,
Resistance Compliance=(Days of Resistance Training/3)+ 2.56667
(b) if said regimen comprises a number of days of resistance training per week which is less than or equal to 4,
Resistance Compliance=Days of Resistance Training.

6. A method for producing an image predictive of a person's appearance resulting from following a prescribed regimen, said method comprising:

receiving a first data set associated with said person;
said first data set comprising a body shape designation;
said body shape designation being representative of where fat is located on said person;

creating a first image representative of said person in a pre-regimen condition by modifying a generic image based on said first data set;

receiving a second data set comprising at least one goal desired from said regimen;

creating a second image representative of said person in a post-regimen condition by modifying said first image based on said second data set; and displaying said second image;

wherein said at least one goal comprises muscle gain and wherein said muscle gain is calculated based on at least one of the following factors:

a base muscle gain factor;
a supplement boost factor;
a resistance compliance factor;
an age factor;
a nutrition factor; and
a gender factor;

wherein said age factor is calculated substantially according to the following equation:

Age Factor=Age$^2$(0.00983)+Age(−1.84086)+ 84.54923.

7. A method for producing an image predictive of a person's appearance resulting from following a prescribed regimen, said method comprising:

receiving a first data set associated with said person;
said first data set comprising a body shape designation;
said body shape designation being representative of where fat is located on said person;

creating a first image representative of said person in a re-regimen condition by modifying a generic image based on said first data set;

receiving a second data set comprising at least one goal desired from said regimen;

creating a second image representative of said person in a post-regimen condition by modifying said first image based on said second data set; and displaying said second image;
wherein said at least one goal comprises muscle gain and wherein said muscle gain is calculated based on at least one of the following factors:
a base muscle gain factor;
supplement boost factor;
a resistance compliance factor;
an age factor;
a nutrition factor; and
a gender factor;
wherein said nutrition factor is calculated substantially according to the following equation:

Nutrition Factor=Days/Week on Nutrition Plan (0.035714286)+0.75.

8. A method for producing an image predictive of a person's appearance resulting from following a prescribed regimen, said method comprising:
receiving a first data set associated with said person;
said first data set comprising a body shape designation;
said body shape designation being representative of where fat is located on said person;
creating a first image representative of said person in a pre-regimen condition by modifying a generic image based on said first data set;
receiving a second data set comprising at least one goal desired from said regimen;
creating a second image representative of said person in a post-regimen condition by modifying said first image based on said second data set; and
displaying said second image;
wherein said at least one goal comprises muscle gain and wherein said muscle gain is calculated based on at least one of the following factors:
a base muscle gain factor;
a supplement boost factor;
a resistance compliance factor;
a age factor;
a nutrition factor; and
a gender factor;
wherein said gender factor is calculated substantially according to one of the following equations:
(a) if said person is a female, Gender Factor$_{female}$=0.55;

(b) if said person is a male,

Gender Factor$_{male}$=1.0.

9. A method for producing an image predictive of a person's appearance resulting from following a prescribed regimen said method comprising:
receiving a first data set associated with said person;
said first data set comprising a body shape designation;
said body shape designation being representative of where fat is located on said person;
creating a first image representative of said person in a pre-regimen condition by modifying a generic image based on said first data set;
receiving a second data set comprising at least one goal desired from said regimen;
creating a second image representative of said person in a post-regimen condition by modifying said first image based on said second data set; and
displaying said second image;
wherein said at least one goal comprises muscle gain and wherein said muscle gain is calculated based on at least one of the following factors:
a base muscle gain factor;
a supplement boost factor;
a resistance compliance factor;
an age factor;
a nutrition factor; and
a gender factor;
wherein said muscle gain is calculated substantially according to the following equation:

Muscle Gained/Week=(Resistance Compliance×Base Muscle Gain Factor) ×Supplement Boost ×Age Factor ×Nutrition Factor ×Gender Factor.

* * * * *

UNITED STATES PATENT AND TRADEMARK OFFICE
CERTIFICATE OF CORRECTION

PATENT NO. : 7,809,153 B2
APPLICATION NO. : 10/684023
DATED : October 5, 2010
INVENTOR(S) : Bravomalo et al.

Page 1 of 1

It is certified that error appears in the above-identified patent and that said Letters Patent is hereby corrected as shown below:

In claim 3, column 20, line 61, delete "a" before the word "appearance".

In claim 3, column 20, line 62, insert a -- , -- after the word "regimen".

In claim 5, column 21, line 56, delete "a" before the word "appearance".

In claim 5, column 22, lines 1-3, replace "creating a second image ... based on said first data set; and" with -- creating a second image representative of said person in a post-regimen condition by modifying said first image based on said second data set; and --.

In claim 5, column 22, lines 5-7, replace "wherein said at least one goal corn rises ... one of the following factors:" with -- wherein said at least one goal comprises muscle gain and wherein said muscle gain is calculated based on at least one of the following factors: --.

In claim 6, column 22, line 51, replace "(0.00983)" with -- (0.009835) --.

In claim 7, column 22, line 61, replace "re-regimen" with -- pre-regimen --.

In claim 8, column 23, line 37, replace "a age factor" with -- an age factor --.

In claim 9, column 24, lines 10-11, insert a -- , -- after the word "regimen".

Signed and Sealed this
Twenty-seventh Day of December, 2011

David J. Kappos
*Director of the United States Patent and Trademark Office*